(12) United States Patent
Rudek et al.

(10) Patent No.: US 10,482,703 B2
(45) Date of Patent: Nov. 19, 2019

(54) EARPLUG DISPENSER WITH ASYMMETRIC MIXING BODY

(71) Applicant: 3M INNOVATIVE PROPERTIES COMPANY, St. Paul, MN (US)

(72) Inventors: David M. Rudek, Dusseldorf (DE); Ralf F. Korte, Sprockhovel (DE); Guenter M. Zilligen, Grevenbroich (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/320,673

(22) PCT Filed: Jun. 17, 2015

(86) PCT No.: PCT/US2015/036232
§ 371 (c)(1),
(2) Date: Dec. 20, 2016

(87) PCT Pub. No.: WO2016/003650
PCT Pub. Date: Jan. 7, 2016

(65) Prior Publication Data
US 2017/0200340 A1 Jul. 13, 2017

Related U.S. Application Data

(60) Provisional application No. 62/019,022, filed on Jun. 30, 2014.

(51) Int. Cl.
*G07F 11/44* (2006.01)
*A61F 15/00* (2006.01)
*A61F 11/08* (2006.01)

(52) U.S. Cl.
CPC .......... *G07F 11/44* (2013.01); *A61F 15/001* (2013.01); *A61F 11/08* (2013.01)

(58) Field of Classification Search
CPC ... A61F 11/08; A61F 15/001; B65D 83/0454; B65D 2583/0418; G07F 11/24; G07F 11/40; G07F 11/54; G07F 11/56
See application file for complete search history.

(56) References Cited

U.S. PATENT DOCUMENTS 920,931 A 5/1909 Donnelly
932,983 A * 8/1909 Grubb ................ B65D 83/0409
221/265

(Continued)

FOREIGN PATENT DOCUMENTS

AU 2006-201162 4/2006
CA 92208 3/1905

(Continued)

OTHER PUBLICATIONS

3M™ E-A-R™ One Touch™ Earplug Dispenser product information webpage, Obtained from the internet on Jul. 16, 2014, URL <http://solutions.3m.com/wps/portal/3M/en_US/3M-PPESafetySolutions/PersonalProtectiveEquipment/Products/ProductCatalog/~/DispensersRefills?N=8690968+5158346+3294529207+3294349995+4294886830&rt=rud>, 2 pages.

(Continued)

*Primary Examiner* — Gene O Crawford
*Assistant Examiner* — Kelvin L Randall, Jr.
(74) *Attorney, Agent, or Firm* — Kenneth B. Wood

(57) ABSTRACT

An earplug dispensing mechanism defining a longitudinal axis, and including separator and index assemblies. The separator assembly includes a platform, a guide wall and bores. The guide wall projects from the platform to define a well for receiving earplugs. The bores each extend from an entrance opening to an exit opening. The index assembly is rotatably coupled to the separator assembly, and includes a handle, a plate, and a mixing body. The plate is connected to the handle and defines a dispensing aperture. The mixing (Continued)

body has an upper end, a lower end, and an exterior surface defined by a cone portion and a paddle portion. The cone portion tapers in diameter. The paddle portion projects radially from the cone portion at the lower end. The exterior surface is asymmetrical to encourage earplug mixing within the well, and to impede earplugs from entering a bore open to the dispensing aperture.

21 Claims, 31 Drawing Sheets

(56) References Cited

U.S. PATENT DOCUMENTS

| | | | |
|---|---|---|---|
| 1,651,605 A | 12/1927 | Kuhn | |
| 1,982,273 A | 11/1934 | Vogel | |
| 2,176,232 A | 10/1939 | Warren | |
| 2,243,335 A * | 5/1941 | Elliott | G07F 11/44 222/184 |
| 2,535,928 A | 12/1950 | Ives | |
| 2,664,223 A * | 12/1953 | Israel | A47F 1/03 221/265 |
| 2,729,366 A * | 1/1956 | Chadwick | B65D 83/0409 222/362 |
| 2,742,200 A | 4/1956 | Marx | |
| 2,772,811 A | 12/1956 | Schaef | |
| 2,880,906 A | 4/1959 | Probasco | |
| 2,886,209 A * | 5/1959 | Lermer | B65D 83/0409 221/287 |
| 3,079,051 A | 2/1963 | Clark | |
| 3,730,387 A | 5/1973 | McConnell | |
| 3,785,525 A * | 1/1974 | Handeland | B65G 47/1471 221/15 |
| 3,811,599 A | 5/1974 | O'Connor | |
| 3,885,703 A | 5/1975 | Neavin | |
| 3,889,847 A * | 6/1975 | Uroshevich | B65D 83/0409 206/540 |
| 3,894,657 A | 7/1975 | Eckmayr | |
| 4,191,308 A | 3/1980 | Allen | |
| 4,273,254 A * | 6/1981 | Cuppleditch | B65D 83/0409 221/196 |
| 4,432,300 A * | 2/1984 | Lyss | A61J 7/04 116/308 |
| 4,483,092 A * | 11/1984 | Steiner | A01K 97/04 221/185 |
| 4,515,063 A | 5/1985 | Lee | |
| 4,782,981 A | 11/1988 | Schuster | |
| 5,014,877 A | 5/1991 | Roos | |
| 5,176,290 A * | 1/1993 | Schwarzli | G07F 11/24 221/200 |
| 5,280,845 A | 1/1994 | Leight | |
| 5,285,925 A | 2/1994 | Leight | |
| 5,318,200 A | 6/1994 | Allen | |
| 5,322,185 A | 6/1994 | Leight | |
| 5,372,278 A | 12/1994 | Leight | |
| 5,791,515 A | 8/1998 | Khan | |
| 5,794,816 A | 8/1998 | Pliler | |
| D413,465 S | 9/1999 | Scholey | |
| D414,359 S | 9/1999 | Scholey | |
| 5,954,229 A | 9/1999 | Scholey | |
| D424,340 S | 5/2000 | Fleming | |
| 6,109,252 A * | 8/2000 | Stevens | F41B 11/53 124/48 |
| 6,241,120 B1 | 6/2001 | Scholey | |
| 6,283,339 B1 | 9/2001 | Morrow | |
| 6,299,019 B1 * | 10/2001 | Leight | A61F 15/001 221/186 |
| 6,604,653 B2 * | 8/2003 | Millar | A61F 11/08 221/203 |
| 7,097,068 B2 * | 8/2006 | Limback | A47L 15/4409 221/2 |
| 7,175,046 B2 | 2/2007 | Yao | |
| 7,735,684 B2 * | 6/2010 | Coe | B65D 83/0409 221/25 |
| 7,810,673 B2 | 10/2010 | Lancesseur | |
| 7,992,748 B2 | 8/2011 | Lawrence | |
| 9,501,890 B2 | 11/2016 | Rudek | |
| 9,550,619 B2 * | 1/2017 | Park, IV | B65D 83/0409 |
| 9,580,230 B2 * | 2/2017 | Dai | B65D 83/0083 |
| 9,828,168 B2 * | 11/2017 | Schmidt-Ellinger | B65B 35/08 |
| 2002/0043538 A1 * | 4/2002 | Millar | A61F 11/08 221/265 |
| 2006/0006189 A1 * | 1/2006 | Curtolo | G21C 19/202 221/178 |
| 2006/0124659 A1 * | 6/2006 | Mosconi | A47J 31/3623 221/161 |
| 2008/0116219 A1 * | 5/2008 | Lawrence | G07F 11/54 221/265 |
| 2008/0173666 A1 * | 7/2008 | Coe | B65D 83/0409 221/265 |

FOREIGN PATENT DOCUMENTS

| | | |
|---|---|---|
| EP | 1035035 | 9/2000 |
| EP | 1739638 | 1/2007 |
| EP | 1772077 | 4/2007 |
| WO | WO 1994-009456 | 4/1994 |
| WO | WO 2002-000155 | 1/2002 |
| WO | WO 2016-003649 | 1/2016 |

OTHER PUBLICATIONS

International Search Report for PCT International Application No. PCT/US2015/036229, dated Sep. 2015, 3 pages.
International Search Report for PCT International Application No. PCT/US2015/036232, dated Sep. 2, 2015, 3 pages.

* cited by examiner

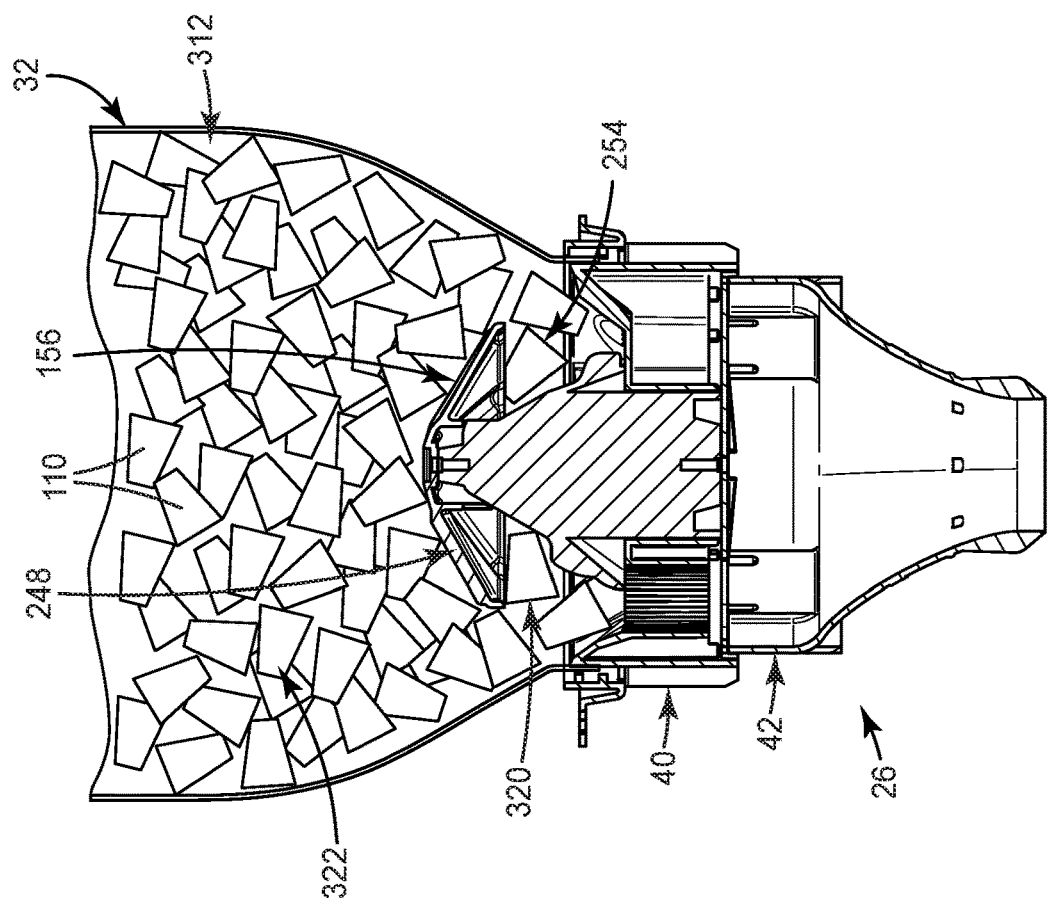
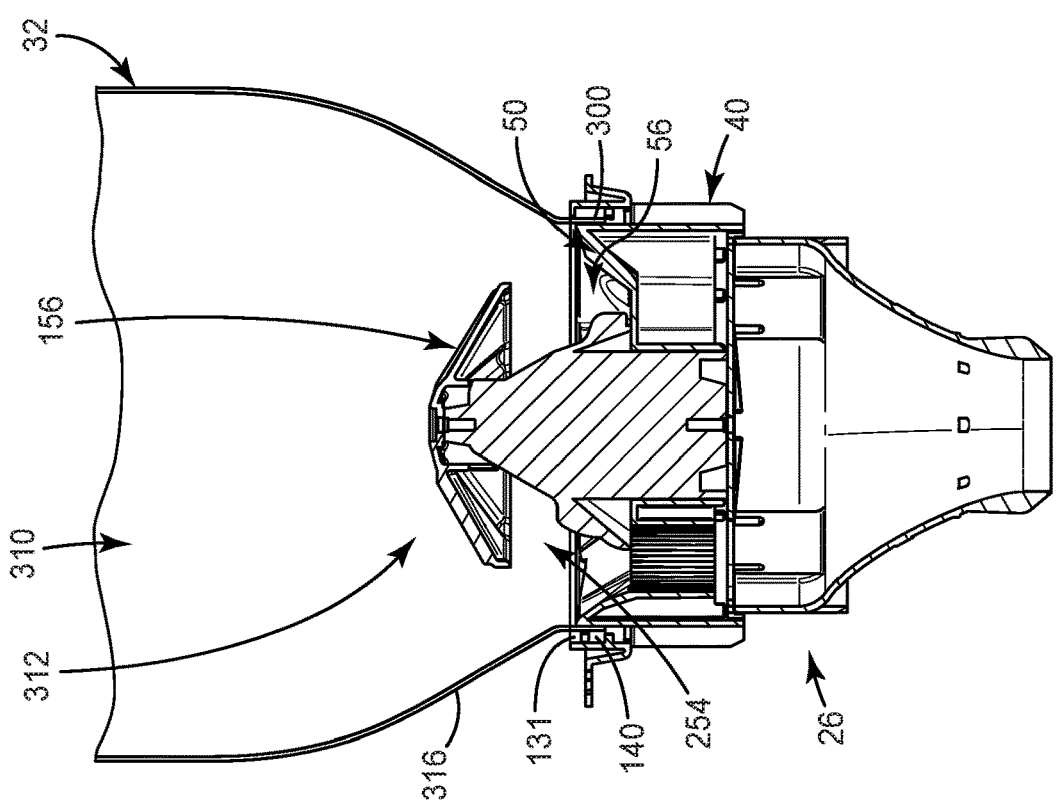
FIG. 15C
FIG. 15B

EARPLUG DISPENSER WITH ASYMMETRIC MIXING BODY

BACKGROUND

The present disclosure relates to product dispensers. More particularly, it relates to manually operable dispensers for storing and dispensing disposable earplugs.

Disposable earplugs are routinely used in a wide variety of settings. In many instances, such as industrial or manufacturing environments, it is highly desirable to have a large quantity of disposable earplugs readily available at all times. Conventionally, disposable earplugs are made available in bulk form, for example by way of a large open box in which the earplugs are loosely maintained. Workers (or other users) simply reach into the box and retrieve earplugs as needed. While viable, the open box format has several distinct drawbacks. For example, a worker will invariably retrieve more than two earplugs when reaching into the box, with the extra, un-needed earplugs often times discarded without being used. Moreover, contaminants in the working environment and/or carried by the worker's hand can be introduced into the open box, leading to possible hygienic concerns.

To address the above concerns, various disposable earplug dispensers have been devised. Typically, the dispenser loosely stores a large, bulk supply of disposable earplugs and provides a manually operable mechanism intended to dispense or vend earplugs one at a time. The dispensing mechanism is conventionally a rotary type, including a wheel forming a series of discrete holes. In theory, earplugs for the bulk supply self-load into respective ones of the holes and then individually dispense from the mechanism, under the force of gravity, with rotation of the wheel. Notably, rotary dispensing mechanisms sometimes employed with earplug dispensers are akin to those found with some medication capsule dispensers or other devices intended to store and individually dispense (or vend) small, hard objects (e.g., gumballs). Given the general similarities between the size and shape of medicinal capsules and disposable earplugs, the apparent usefulness of this rotary mechanism format is well-based. However, certain physical characteristics unique to disposable earplugs present distinct concerns not fully addressed by conventional rotary-type dispensing mechanisms.

For example, some types of disposable earplugs are formed of a slow-recovery foam material, open cell or closed surface and, unlike hard objects, are compressible. Further, most disposable earplugs exhibit some degree of tackiness at their outer surface. These unique characteristics make it difficult for a conventional rotary-type dispensing mechanism to accurately and consistently dispense only a single earplug with each user-caused wheel rotation. Instead, two (or more) earplugs will self-load into a single dispensing hole and subsequently dispense in tandem; alternatively, the bulk supply will overtly prevent any one earplug from self-loading into a dispensing hole. Further, malfunctions can be prevalent, with the compressible earplugs easily becoming lodged between various moving components of the dispensing mechanism.

In light of the above, a need exists for disposable earplug dispensers, and related manually operable dispensing mechanisms, that accurately dispense earplugs one at a time with minimal instances of jamming or other malfunctions.

SUMMARY

Some aspects of the present disclosure are directed toward a manually operable dispenser for dispensing earplugs from a container of earplugs. The dispenser includes a dispensing mechanism defining a longitudinal axis and comprising a separator assembly and an index assembly. The separator assembly includes a platform, a guide wall and a plurality of circumferentially arranged bore structures. The guide wall projects from the platform to define a well for receiving earplugs from a container of earplugs. The bore structures each form a bore extending from an entrance opening in the platform to an exit opening at a trailing side opposite the platform. The index assembly is rotatably coupled to the separator assembly, and includes a handle, a plate, and a mixing body. The plate is connected to the handle and defines a dispensing aperture. The mixing body is connected to the plate opposite the handle. The mixing body has an upper end, a lower end, and an exterior surface defined, at least in part, by a cone portion and a paddle portion. The cone portion forms the exterior surface to taper in diameter from the lower end toward the upper end. The paddle portion projects radially, relative to the longitudinal axis, from the cone portion at the lower end. The exterior surface is asymmetrical. At least the lower end of the mixing body is disposed within the well. The dispensing mechanism is configured such that a manually-applied rotational force at the handle selectively aligns the dispensing aperture with the exit opening of individual ones of the bores, and selectively arranges the paddle portion to at least partially cover the entrance opening of individual ones of the bores. The asymmetrical shape encourages mixing of free earplugs within the well, and impedes earplugs from entering a bore otherwise aligned with the dispensing aperture. In some embodiments, the paddle portion is aligned with, and rotates in tandem with, the dispensing aperture.

BRIEF DESCRIPTION OF THE DRAWINGS

FIG. 15B is a cross-sectional view of a portion of the dispensing mechanism and container of FIG. 15A upon final assembly;

FIG. 15C is a cross-sectional view of the assembly of FIG. 15B and loaded with disposable earplugs;

DETAILED DESCRIPTION

Figure 1A:
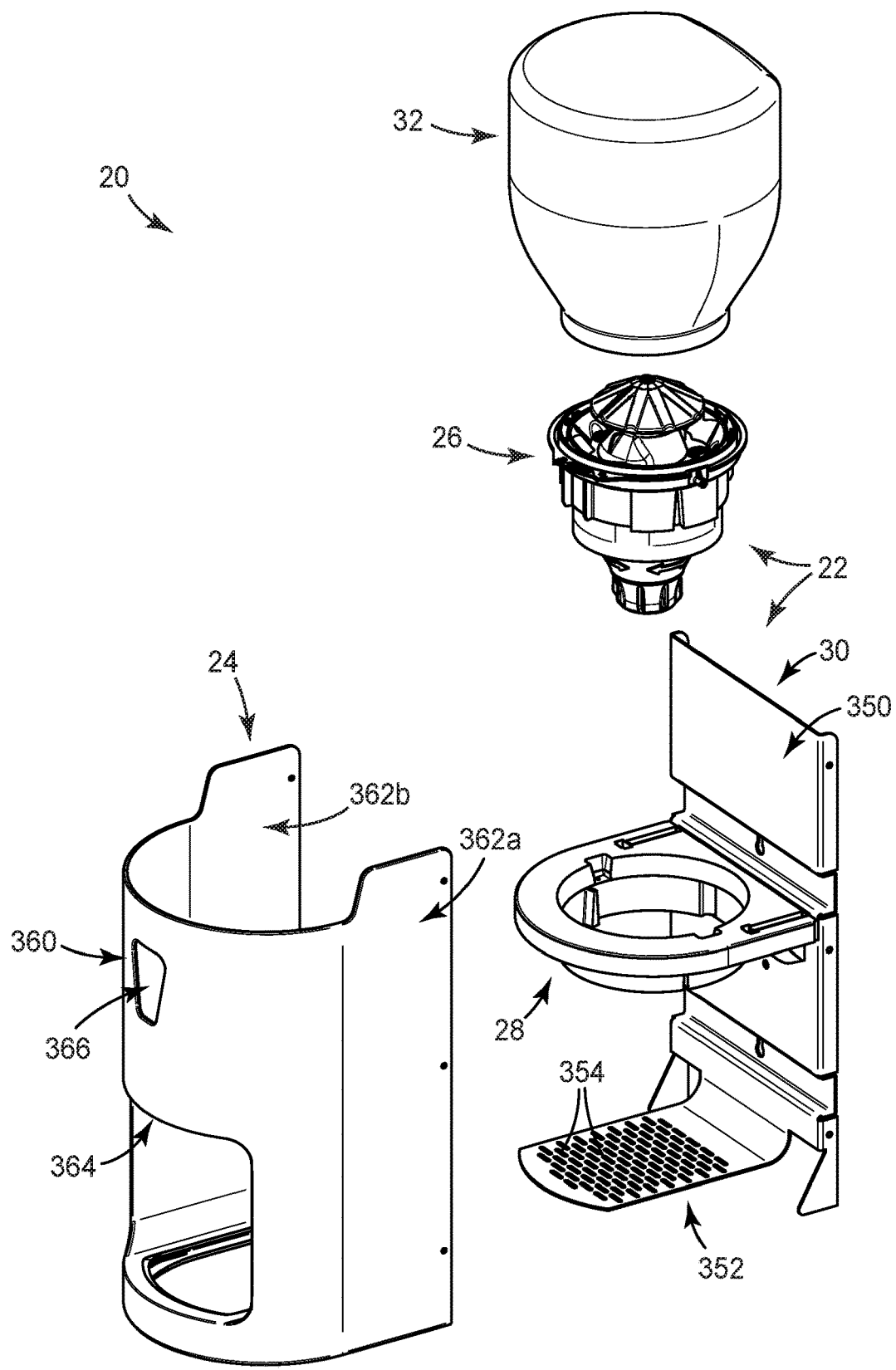
FIG. 1A is a perspective, exploded view of an earplug dispenser in accordance with principles of the present disclosure, along with a container.
Figure 1B:
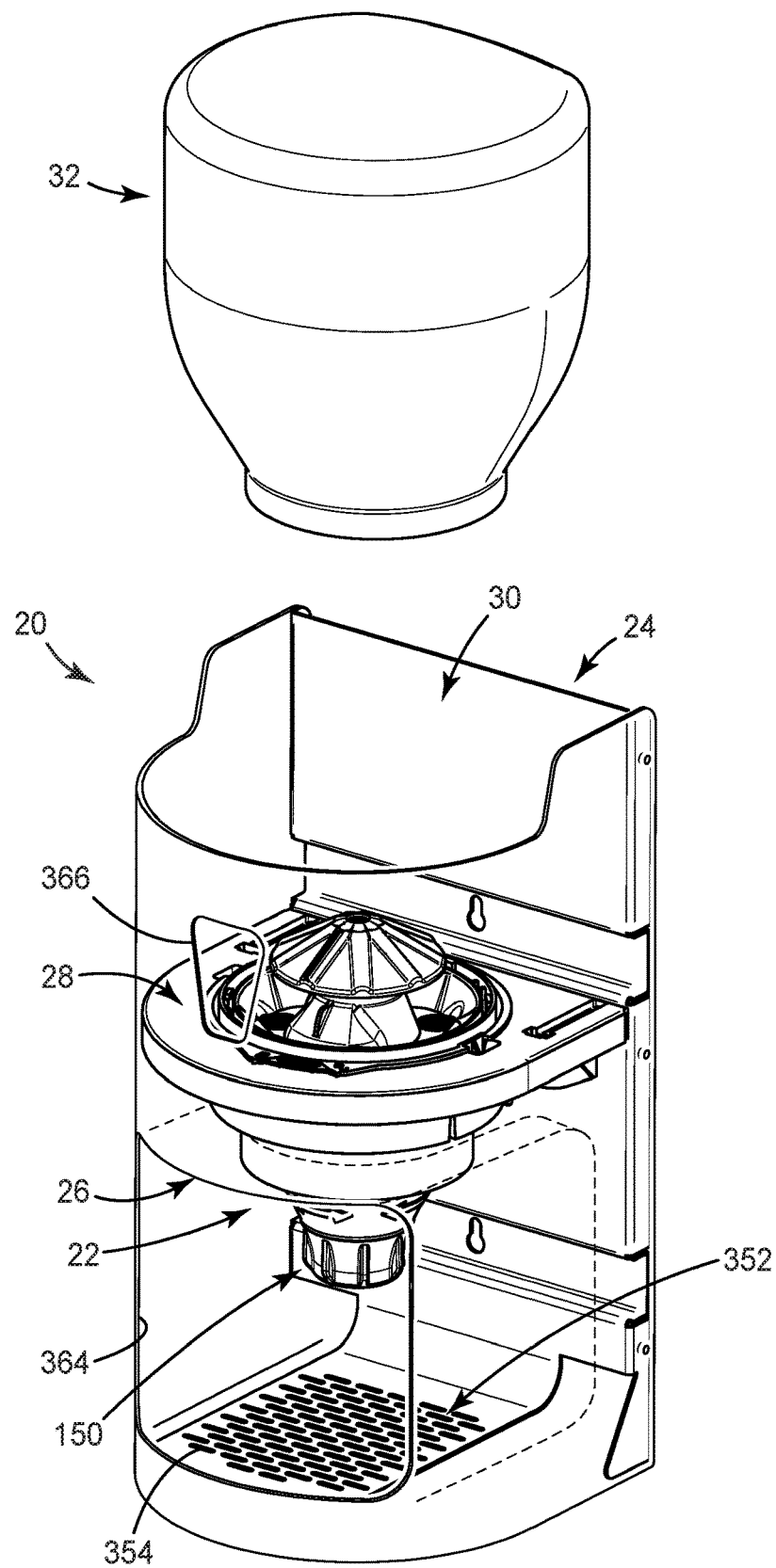
FIG. 1B is a perspective view of the dispenser of FIG. 1A upon final assembly, along with the container.

One embodiment of an earplug dispenser 20 in accordance with principles of the present disclosure is shown in FIGS. 1A and 1B. The dispenser 20 includes a dispensing unit 22 and an optional cover 24 (portions of which are illustrated as being transparent in FIGS. 1A and 1B). The dispensing unit 22, in turn, includes a dispensing mechanism 26 and a frame 28 maintained by an optional stand 30. Details on the various components are provided below. In general terms, however, the dispensing mechanism 26 is configured to receive a container 32 containing a bulk supply of disposable earplugs (not shown), and is manually operable to individually dispense earplugs from the bulk supply. The frame 28 retains the dispensing mechanism 26, with the optional stand 30 supporting the frame 28, and thus the dispensing mechanism 26, relative to an installation surface (e.g., wall, table top, etc.). Where provided, the cover 24 partially shields the individual earplugs from the surrounding environment as they are released from the dispensing mechanism 26. The dispenser 20, and in particular the dispensing mechanism 26, is configured to interface with and accurately dispense compressible, tacky surface earplugs with minimal occurrences of mechanism jamming.

Figure 2A:
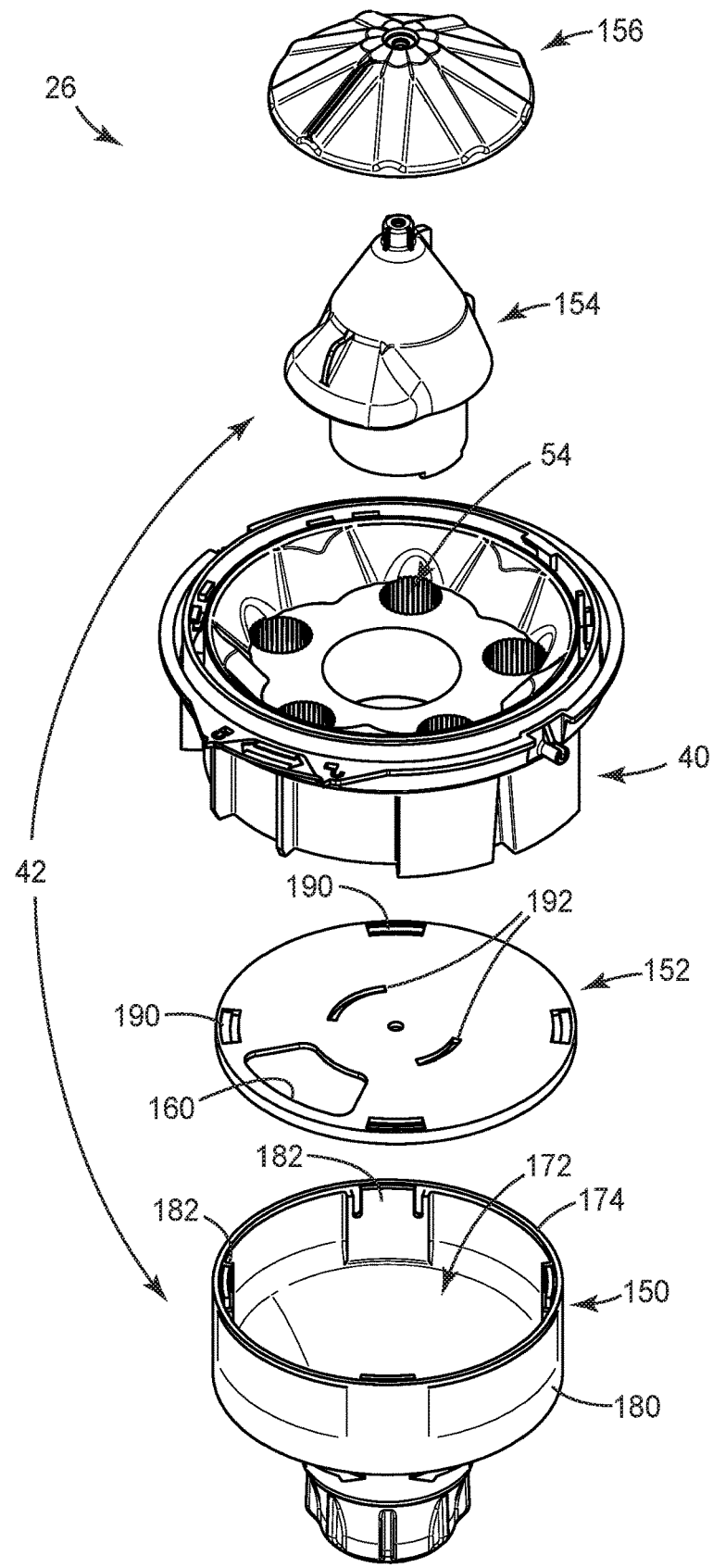
FIG. 2A is a perspective, exploded view of a dispensing mechanism in accordance with principles of the present disclosure and useful with the dispenser of FIG. 1A, including a separator assembly and an index assembly.
Figure 2B:
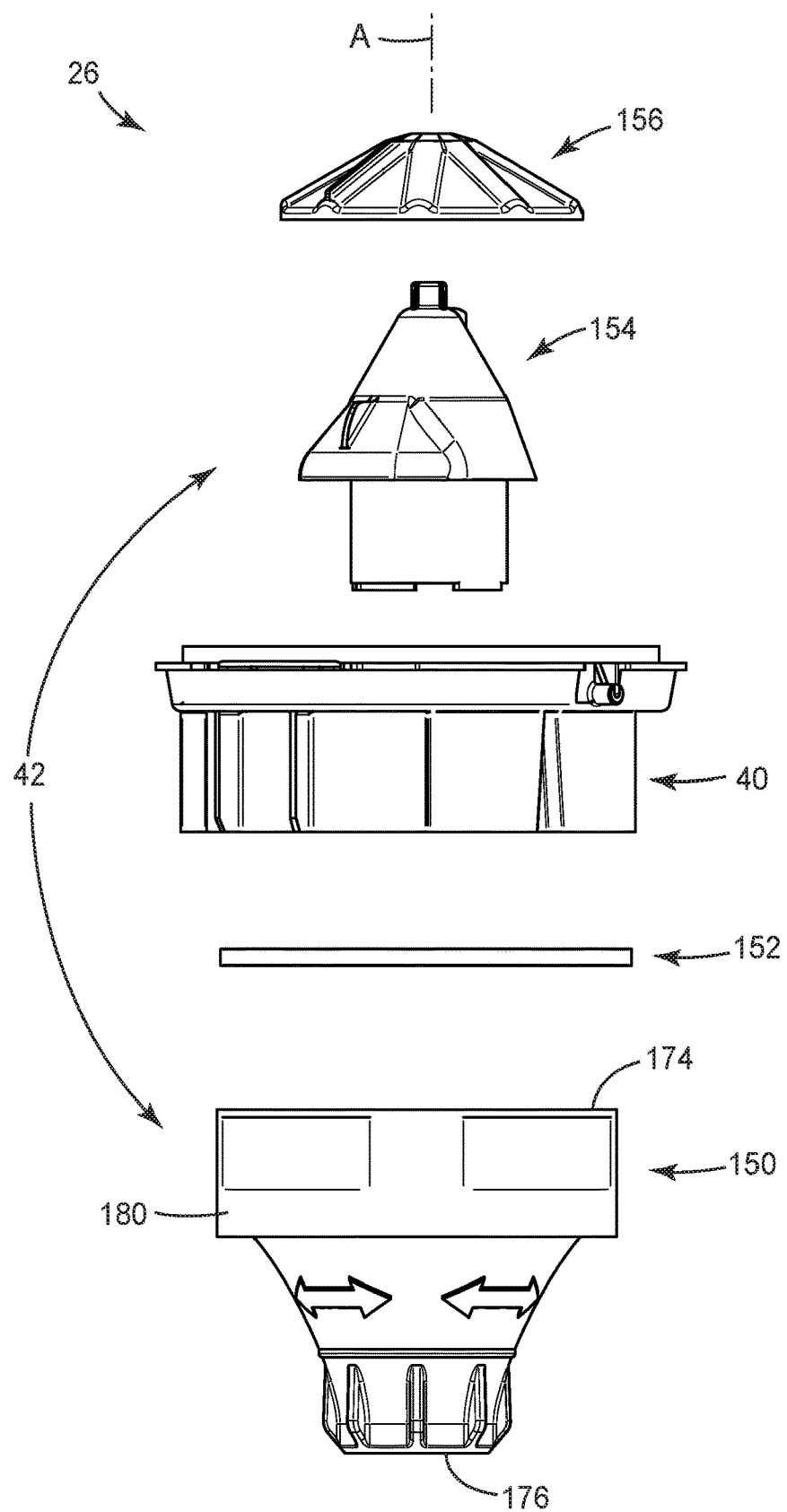
FIG. 2B is a side, exploded view of the dispensing mechanism of FIG. 2A.

One embodiment of the dispensing mechanism 26 is shown in greater detail in FIGS. 2A and 2B, and includes a separator assembly 40 and an index assembly 42 (referenced generally). In general terms, the index assembly 42 is rotatably coupled to the separator assembly 40 such that the index assembly 42 is rotatable relative to the separator assembly 40 about a longitudinal axis A. Several features optionally provided by the assemblies 40, 42 are described below with reference to the longitudinal axis A.

Figure 3A:
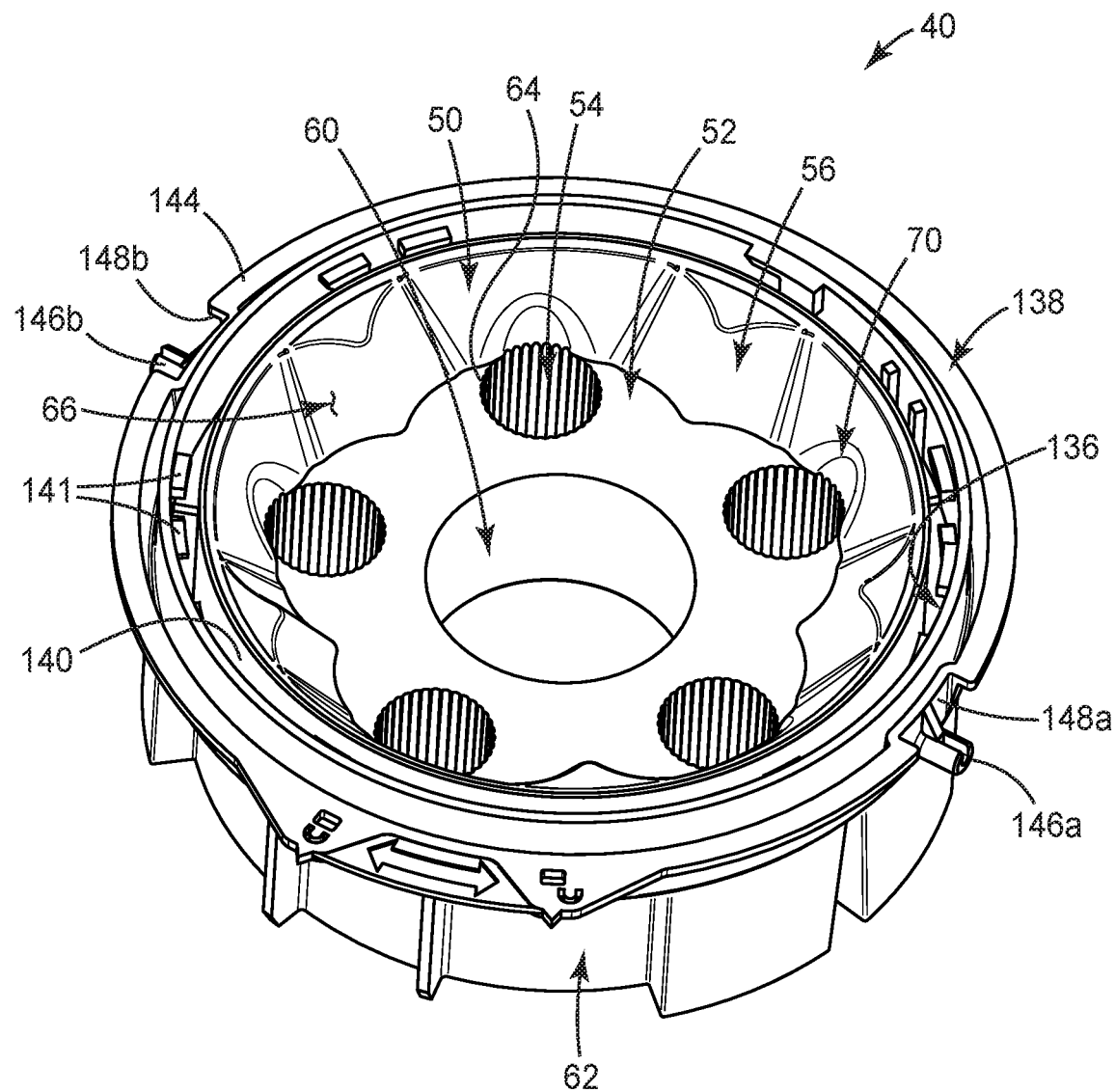
FIG. 3A is a top perspective view of the separator assembly of FIG. 2A.
Figure 3B:
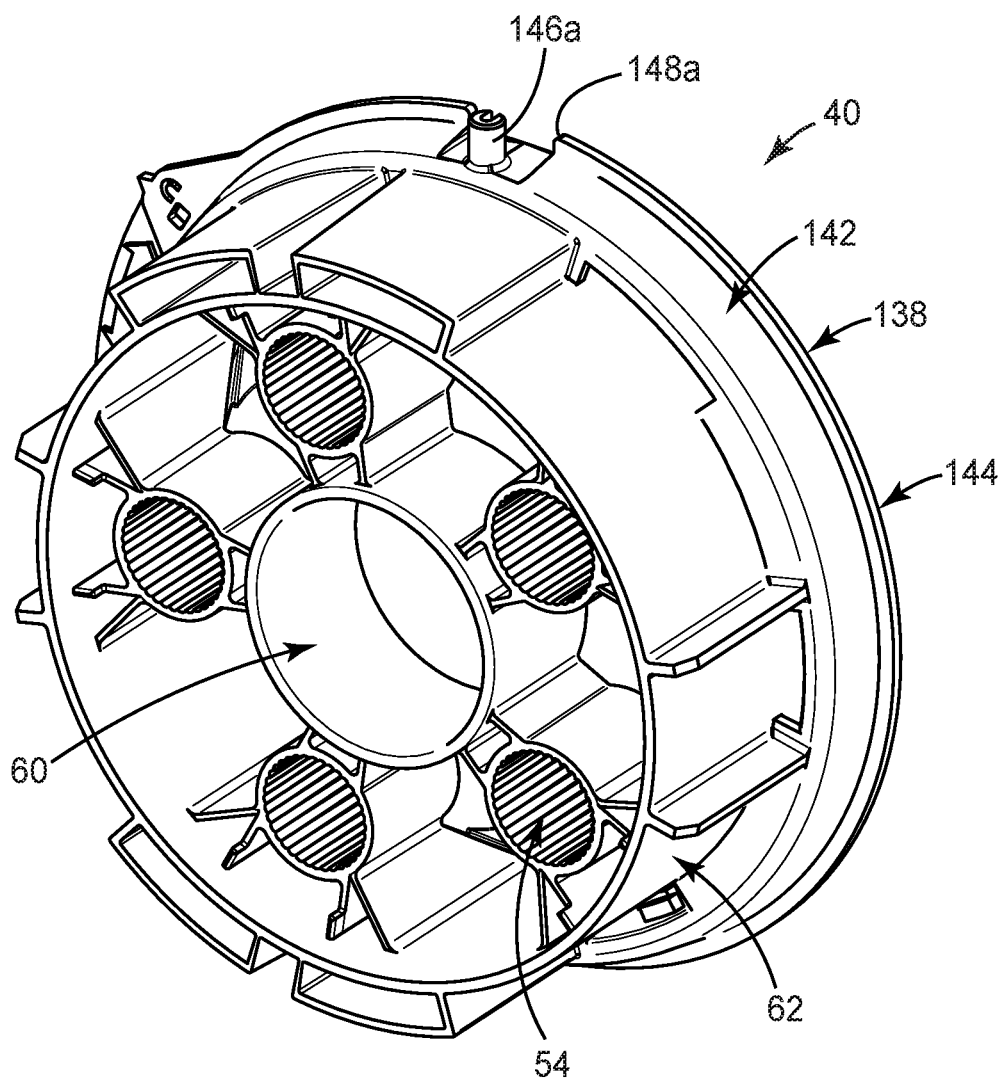
FIG. 3B is a rear perspective view of the separator assembly of FIG. 3A.
Figure 3C:
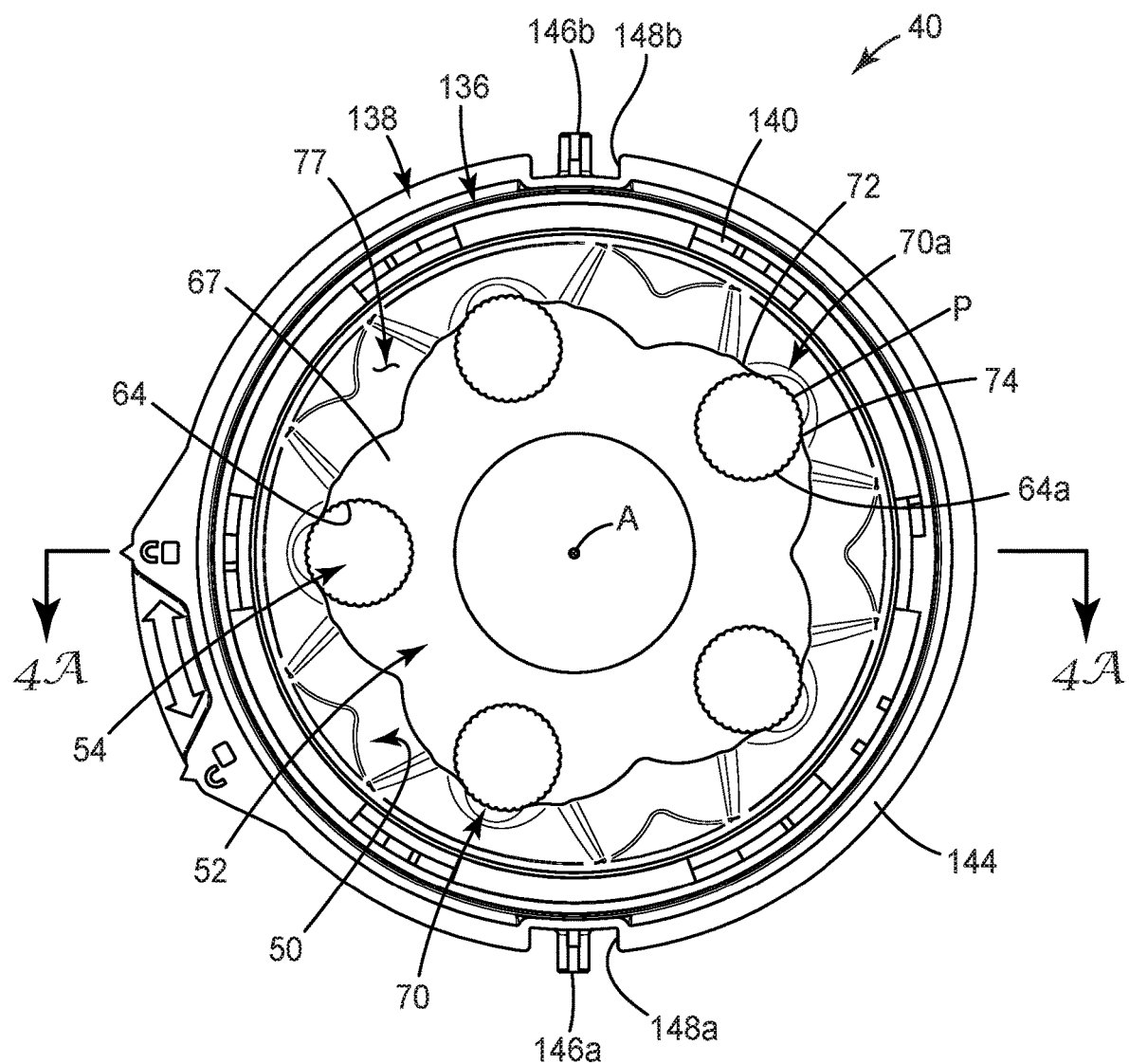
FIG. 3C is a top plan view of the separator assembly of FIG. 3A.

An exemplary embodiment of the separator assembly 40 is shown in greater detail in FIGS. 3A-3C, and includes or defines a guide wall 50, a platform 52, and a plurality of bores 54. The guide wall 50 extends from the platform 52, with the platform 52 and the guide wall 50 combining to define a well 56 (referenced generally in FIGS. 3A and 3C) within which earplugs (not shown) can accumulate. The bores 54 are each open to the well 56 at the platform 52, and are configured to receive individual ones of the earplugs as described below. The separator assembly 40 further includes features that promote coupling with the index assembly 42 (FIG. 2A) and the frame 28 (FIG. 1A), such as an inner hub 60 and an outer hub 62.

The guide wall 50 is generally configured to contain randomly arranged earplugs (not shown) on the platform 52 (and within the well 56), and optionally incorporates one or more features that assist in directing individual earplugs into respective ones of the bores 54 and/or enhances mixing of the randomly arranged earplugs within the well 56 during operation of the dispensing mechanism 26 (FIG. 2A). As a point of reference, and as described in greater detail below, operation of the dispensing mechanism 26 entails rotating the index assembly 42 (FIG. 2) relative to the separator assembly 40 to release an individual earplug from a respective one of the bores 54. A new earplug (from the grouping of earplugs within the well 56) then self-loads into the now-empty bore 54 via a corresponding entrance opening 64 in the platform 52. The guide wall 50 can assist in directing the individual earplug to the entrance opening 64 in a desired orientation. Further, the index assembly 42 can include various features that interact with the grouping of earplugs within the well 56 upon rotation of the index assembly 42, with this interaction desirably mixing, or reorienting, many of the earplugs within the grouping; the guide wall 50 optionally incorporates features that enhance the mixing effect caused by rotation of the index assembly 42.

Figure 4A:
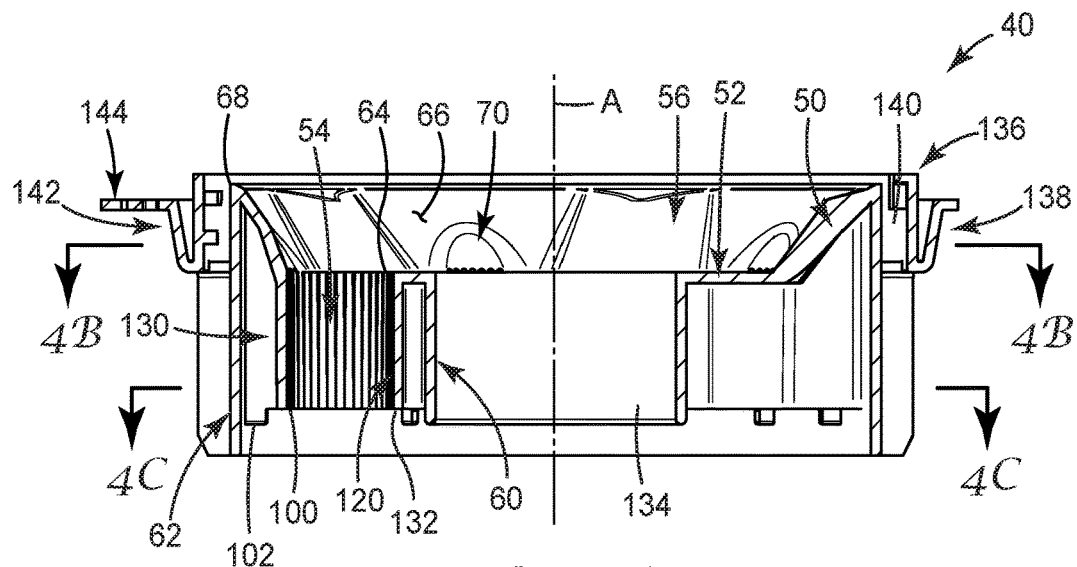
FIG. 4A is a cross-sectional view of the separator assembly of FIG. 3C, taken along the line 4A-4A.

With the above operational attributes in mind, FIG. 3C reflects that the guide wall 50 defines a continuous, interior or guide face 66 that contacts earplugs (not shown) within the well 56. In a plane perpendicular to the longitudinal axis A, the guide face 66 has a closed shape that exteriorly surrounds the entrance openings 64. With additional reference to FIG. 4A, the guide wall 50 projects upwardly (relative to the orientation of FIG. 4A) from the platform 52, terminating at an upper edge 68 (at an intersection of the guide wall 50 with the outer hub 62). In some embodiments, the guide face 66 has a radially inward (relative to the longitudinal axis A) taper from the upper edge 68 to the platform 52. For example, the closed shape of the guide face 66 can be described as defining a diameter in a plane corresponding with the longitudinal axis A (e.g., the plane of the cross-section of FIG. 4A); FIG. 4A illustrates that the diameter of the shape defined by the guide face 66 generally decreases from the upper edge 68 to the platform 52. This optional tapering configuration of the guide face 66 enlarges a volume of the well 56 (as compared to configurations in which the guide wall 50 projects from the platform 52 at a right angle) while directing or guiding earplugs (not shown) within the well 56 toward the entrance openings 64.

As further reflected by FIG. 3A, a plurality of troughs 70 are optionally formed in the guide face 66, with respective ones of the troughs 70 being aligned with corresponding ones of the entrance openings 64. The troughs 70 are each sized and shaped to guide a single earplug (not shown), otherwise in contact with the trough 70, directly toward the corresponding entrance opening 64 in an upright or lengthwise orientation described below. For example, FIG. 3C identifies certain features of the guide face 66 relative to the trough 70*a* and the corresponding entrance opening 64*a*. Relative to the longitudinal axis A, the entrance opening 64*a* can be described as having or defining a radially outermost point P. At the point of intersection with the platform 52, the guide face 66 is optionally in highly close proximity to the entrance opening 64*a*. In some embodiments, the guide face 66 can be described as forming opposing guide segments 72, 74 at opposite sides of the trough 70*a*. The guide segments 72, 74 terminate at an edge of the entrance opening 64*a*. The trough 70*a* also terminates at an edge of the entrance opening 64*a* (including at the radially outermost point P), with the radially outermost point P of the entrance opening 64*a* being radially beyond (relative to the longitudinal axis A) the guide segments 72, 74. With this construction, the guide face 66 (i.e., the trough 70*a* and the guide segment 72, 74) partially surround, but do not obstruct, the entrance opening 64*a*. Thus, an earplug bearing against the guide face 66 at the trough 70*a* is guided directly into the entrance opening 64*a*. The guide face 66 can alternatively have other constructions that may or may not partially surround one or more of the entrance openings 64 and/or that may or may not include the troughs 70.

Figure 4B:
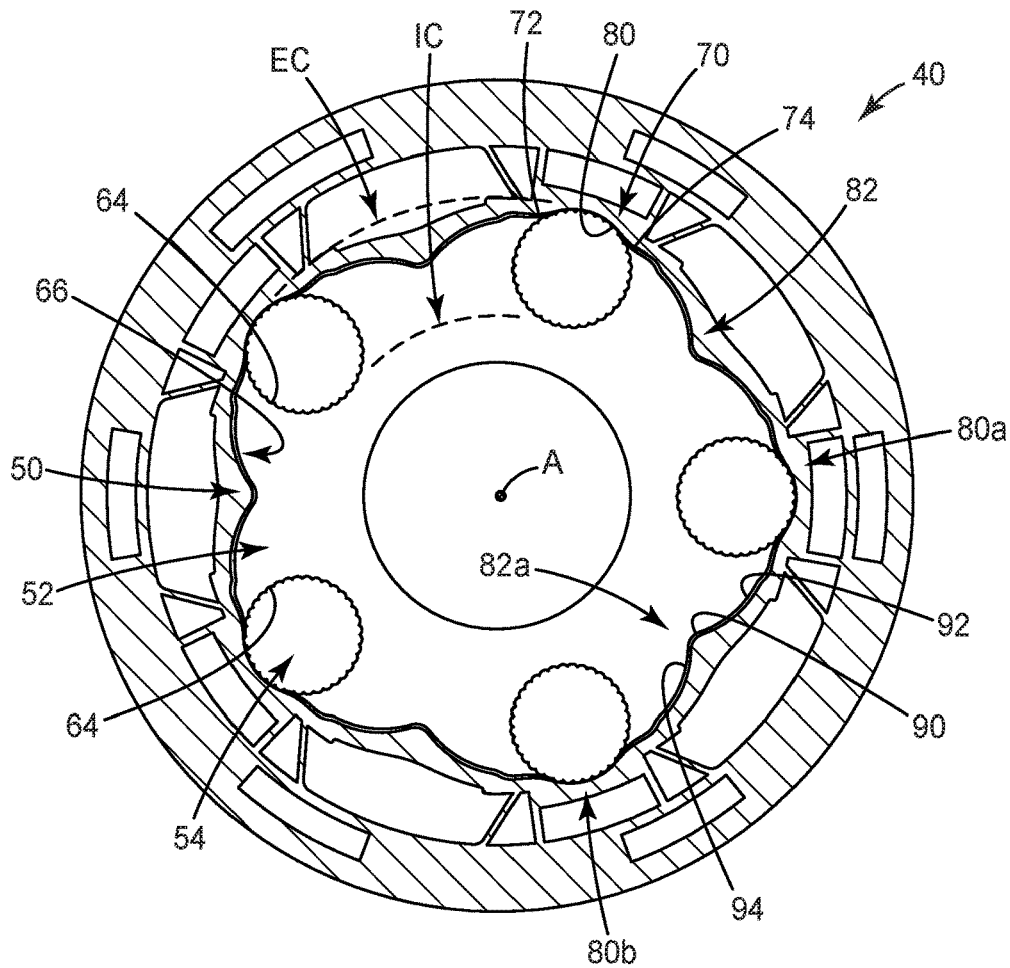
FIG. 4B is a cross-sectional view of the separator assembly of FIG. 4A, taken along the line 4B-4B.

Other optional geometric features of the guide face 66 are best described with reference to the cross-sectional view of FIG. 4B (otherwise taken in a plane perpendicular to the longitudinal axis A). Once again, the guide wall 50 forms the guide face 66 to define a closed shape in a plane perpendicular to the longitudinal axis A. The closed shape is generally circular, and in some embodiments is a closed, compound curved shape (i.e., is not true circle), at least at a point or plane of intersection with the platform 52. The exemplary closed shape of the guide face 66 in a plane perpendicular to the longitudinal axis A is a wavy shape. In some embodiments, the closed shape of the guide face 66 in the perpendicular plane can be described as having or forming a plurality of ramp regions 80 and a plurality of channel regions 82. Respective ones of the ramp regions 80 are aligned with a corresponding one of the entrance openings 64 (e.g., relative to a direction radial or perpendicular to the longitudinal axis A, each ramp region 80 is radially aligned with a corresponding one of the entrance openings 64). The channel regions 82 are interposed between circumferentially adjacent ones of the ramp regions 80 (e.g., as identified in FIG. 4B, the channel region 82*a* is interposed between the circumferentially adjacent ramp regions 80*a*, 80*b*). In general terms, the ramp regions 80 are each configured to guide an individual earplug (not shown) into the corresponding entrance opening 64, and the channel regions 82 are each configured to direct earplugs toward the corresponding ramp region(s) 80 and enhance mixing of earplugs within the well 56.

Geometric features associated with the ramp and channel regions 80, 82 can optionally be described with respect to an arrangement of the entrance openings 64. In some embodiments, the entrance openings 64, as formed in or by the platform 52, are circumferentially aligned with one another.

Further, the entrance openings 64 each have an identical, or substantially identical (e.g., within 5% of identical), diameter. With this construction, the entrance openings 64 collectively define an imaginary ring shape having an interior circumference IC and an exterior circumference EC (represented in FIG. 4B by hypothetical, or imaginary, dashed lines). At least a portion of each of the ramp regions 80, at the point or plane of intersection with the platform 52, is at or radially beyond (relative to the longitudinal axis A) the exterior circumference EC. For example, the ramp region 80 optionally forms or includes one of the troughs 70 (FIG. 3C); commensurate with the above descriptions, the trough 70 terminates (i.e., intersects the platform 52) at or immediately outside of the corresponding entrance opening 64, and thus is at or slightly radially beyond the exterior circumference EC. Other portions (e.g., the guide segments 72, 74) of the ramp region 80 can project into the circumferential spacing between immediately circumferentially adjacent ones of the entrance openings 64, and thus are between the exterior and interior circumferences EC, IC (i.e., portions of the ramp region 80 are radially (relative to the longitudinal axis A) inside of the exterior circumference EC). In some embodiments, the troughs 70 each have a symmetrical shape, and are each centered about the corresponding entrance opening 64.

Regardless of an exact structure of the ramp regions 80, the channel regions 82 each represent a more pronounced, radially inward (relative to the longitudinal axis A) projection of the guide face 66. For example, relative to the longitudinal axis A, a radius of the closed shape along at least a portion of each channel region 82 is less than a radius of the closed shape along at least a portion of each ramp region 80. Alternatively, at least a portion of each channel region 82 extends to a location radially inward (i.e., in a direction of the longitudinal axis A) of any portion of the ramp regions 80. In other terms, at least a portion of each channel region 82 projects radially between the interior and exterior circumferences IC, EC, and is more proximate the interior circumference IC and/or the longitudinal axis A than any portion of the ramp regions 80. With this construction, the channel regions 82 each occupy space between circumferentially adjacent ones of the entrance openings 64, serving to funnel earplugs (not shown) in the well 56 toward the corresponding ramp regions 80 (and thus the corresponding entrance openings 64). Further, by projecting into the spacing between circumferentially adjacent entrance openings 64, the channel regions 82 each more readily interface with earplugs within the well 56 as the grouping of earplugs is subjected to rotational forces of the index assembly 42 (as compared to a level of interface were the closed shape of the guide face 66 to instead be a right cylinder), thereby enhancing mixing of the earplugs within the grouping.

The channel regions 82 can assume a wide variety of constructions or shapes having a radially inward (relative to the longitudinal axis A) projection component, and in some embodiments are identical. For example, and as identified for the channel region 82*a* in FIG. 4B, the guide face 66 can be described as defining (in a plane perpendicular to the longitudinal axis A at least at the platform 52) each of the channel regions 82 to include a central segment 90 and opposing, first and second side segments 92, 94. The first and second side segments 92, 94 each extend from opposing ones of the ramp regions 80 (e.g., relative to the channel regions 82*a* identified in FIG. 4B, the first side segment 92 extends from the ramp region 80*a*, and the second side segment 94 extends from the ramp region 80*b*) to the central segment 90. Relative to a plane perpendicular to the longitudinal axis A (e.g., the plane of FIG. 4B), the side segments 92, 94 can be identical in terms of size and shape, each forming a concave curve. In other terms, the first side segment 92 can be a mirror image of the second side segment 94 relative to the central segment 90. Regardless, a shape or radial projection of the side segments 92, 94 locates the central segment 90 more proximate the longitudinal axis A (as compared to the ramp regions 80). The central segment 90 can have a variety of shapes (in a plane perpendicular to the longitudinal axis A), such as the triangle or triangular shape reflected by FIG. 4B. Other shapes (rounded, rectangular, compound curved, etc.) are also acceptable. In alternative embodiments of the present disclosure, the closed shape defined by the guide face 66 can assume other forms that may or may not be directly implicated by the FIGURES, including shapes that do not include one or both of the ramp and channel regions 80, 82.

Returning to FIGS. 3A-4B, the platform 52 can be a substantially planar body, extending between the inner hub 60 and the guide wall 50. The platform 52 serves to define a bottom or lower surface of the well 56, as well as the entrance opening 64 of each of the bores 54.

While the views reflect the separator assembly 40 as providing five of the bores 54, any other number, either greater or lesser, is equally acceptable. The bores 54 are arranged to extend in the longitudinal direction (e.g., a central axis of each of the bores 54 is substantially parallel (e.g., within 5 degrees of a truly parallel relationship) with the longitudinal axis A), from the entrance opening 64 to an exit opening 100. Relative to the orientation of FIG. 4A, then, earplugs (not shown) are initially loaded into the bores 54 from "above" the platform 52, and are dispensed or released to a location "below" the exit openings 100. In this regard, the platform 52 can be viewed as defining an upper major face of the separator assembly 40. In some embodiments, the separator assembly 40 can have a generally hollow construction, with the outer hub 62 defining a lower major face 102 of the separator assembly 40 opposite the platform 52. In other embodiments, the separator assembly 40 can have a more solid construction. Regardless, and as described in greater detail below, individual earplugs will self-load into each of the bores 54 at the platform 52, followed by gravity-induced release of an individual earplug from the corresponding bore 54 in a direction of the lower major face 102.

The bores 54 can each have the cylindrical shape as shown. In other embodiments, the bores 54 can have a tapering shape, either increasing or decreasing in diameter in extension from the platform 52. In yet other embodiments, the bores 54 can be non-circular in transverse cross-section, for example having an oval-like perimeter shape.

Figure 5A:
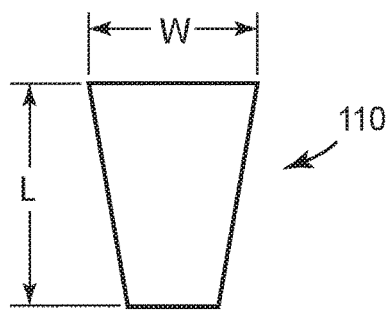
FIG. 5A is a simplified side view of a disposable earplug.
Figure 5B:
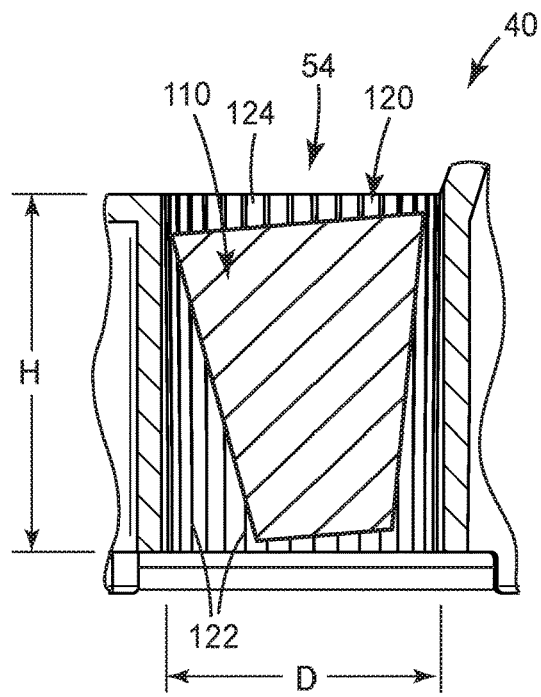
FIGS. 5B and 5C are enlarged, cross-sectional views of a portion of the separator assembly of FIG. 3A, and illustrate an interface between a disposable earplug and a bore provided with the separator assembly.
Figure 5C:
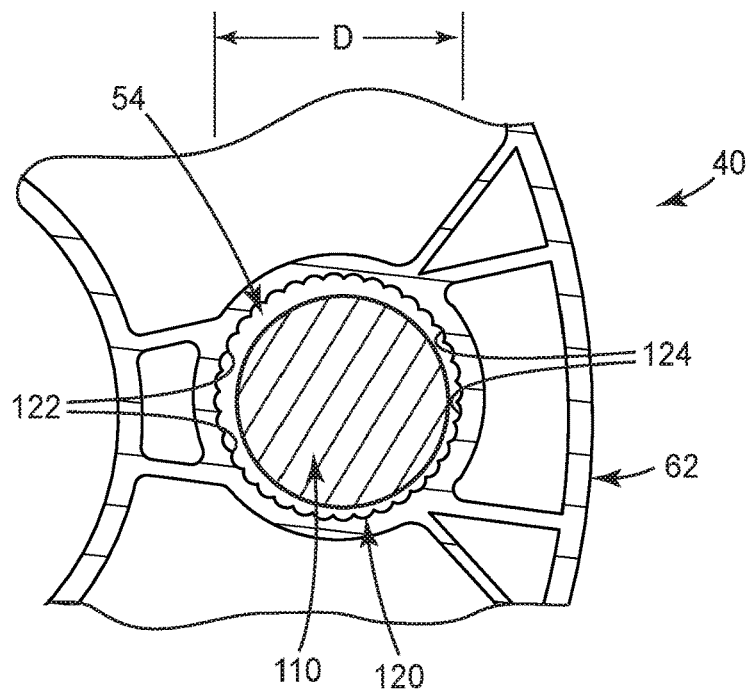

The bores 54 are generally sized and shaped to promote temporary retention of an individual earplug in an upright or lengthwise orientation. As a point of reference, disposable earplugs useful with the dispensers of the present disclosure can have a variety of different constructions (e.g., shapes, dimensions, materials, etc.), and the bores 54 are configured to accurately interface or handle a number of differently configured earplug designs, styles or formats. In more general terms, however, and with reference to FIG. 5A, a disposable earplug 110 defines a length L and a maximum outer width (or diameter) W. The length L is conventionally greater than the maximum width W such that FIG. 5A depicts the earplug 110 in an upright or lengthwise direction (i.e., a major axis defined by a shape of the earplug 110 is arranged vertically). Disposable earplugs useful with the present disclosure can have a variety of different shapes, such as the conical-like shape shown in FIG. 5A, or other shapes such as cylindrical or cylindrical-like, or a more complex shape. The present disclosure is not limited to any particular disposable earplug shape or size. With this in mind, FIGS. 5B and 5C illustrate that each of the bores 54 has a height H and minimum diameter D selected in accordance with the expected earplug length L and maximum width W, and in particular such that the earplug 110 can only be completely received and arranged within the bore 54 in the lengthwise direction. The bore diameter D is less than the expected length L of the earplug 110 so that the loaded earplug 110 occupies a majority of the height H, thus preventing a second earplug (not shown) from completely loading into the bore 54 "on top of" the already-loaded earplug 110 (and thus only a single earplug 110 will subsequently be dispensed from the bore 54). Stated otherwise, were the bore 54 sized so that the earplug 110 could be arranged horizontally within the bore 54 (or perpendicular to the height H of the bore 54), a second earplug could undesirably also fully load within the bore 54. However, the bore diameter D is at least slightly greater than the expected earplug maximum width W to permit the earplug 110 to readily enter or load within the bore 54 in the lengthwise orientation. In this regard, in some embodiments the dispensers of the present disclosure are configured to be equally useful with a number of different earplug shapes and sizes (e.g., eleven different disposable earplug formats), with the bore diameter D selected to be slightly greater than the largest earplug diameter from the earplug products intended to be used with the particular dispenser. The dimensional relationship between the bore 54 and the earplug 110 reflected in the views of FIGS. 5B and 5C (in which the earplug 110 occupies a significant portion of the bore height H and diameter D) is but one example. Dispensers and dispensing mechanisms of the present disclosure are equally useful with other earplug sizes, including those that are smaller than the earplug 110 illustrated. Thus, other earplugs may be shorter (and thus occupy less of the bore height H) and/or more narrow (and thus occupy less of the bore diameter D) as compared to the relative sizes of FIGS. 5B and 5C.

As identified in FIGS. 5B and 5C, each of the bores 54 is generated or circumscribed by a wall surface 120. While in theory it may be possible for the individual earplug 110 to reside within a corresponding one of the bores 54 without contacting the wall surface 120 of the bore 54, in actual practice, the earplug 110 will be in virtually constant contact with various regions of the wall surface 120. With this in mind, in some embodiments the wall surface 120 optionally incorporates one or more anti-bonding constructions or features that promote low friction interface with the disposable earplug 110. More particularly, the wall surface 120 is optionally configured to promote sliding interface with an outer surface of the earplug 110 that may be at least somewhat tacky or sticky. The sliding interface can be provided by forming a macroscopic roughness at or on at least a portion of the wall surface 120. For example, in some embodiments the wall surface 120 forms or defines a plurality of longitudinal ribs 122. The ribs 122 collectively form a ribbed macrostructure, with circumferentially adjacent ones of the ribs 122 being separated by a groove 124. A radial height of each of the ribs 122 (and thus a depth of each of the grooves 124) can be on the order of at least 0.3 mm, although other dimensions (either greater or lesser) are also acceptable. The ribs 122 can be uniformly formed about a circumference of the wall surface 120, with a circumferential width of each of the grooves 124 being on the order of not less than 1 mm although other dimensions (either greater or lesser) are also acceptable. The ribs 122 can generally follow the intended drop direction of the earplug 110 (e.g., are substantially parallel (e.g., within 5% of a truly parallel relationship) with a center line of the bore 54 and thus with the longitudinal axis A (FIG. 4A)). Alternatively, the ribs 122 can be arranged at an angle relative to the bore center line, defining a slight spiral or twist or rifling in extension between opposing ends of the wall surface 120. Finally, while the ribs 122 have been illustrated as being formed or provided along an entirety of the wall surface 120 (e.g., extending between the platform 52 and an opposing, terminal end of the bore 54), in other embodiments the ribs 122 (or other earplug interface surface enhancing feature) can encompass only a portion of the wall surface 120.

In other embodiments, the ribs 122 are replaced by another form of macroscopic surface texturing or roughening (e.g., the wall surface 120 can be knurled), or formed by a series of bumps or rings or other shaped protrusions configured to provide a low friction interface with a disposable earplug in contact therewith. In yet other embodiments, the optional anti-bonding construction or feature provided with the wall surface 120 includes coating or forming the wall surface 120 with a low surface energy material to reduce adhesive forces between the earplug 110 and the wall surface 120 (e.g., a low surface energy material is one that exhibits a tendency to repel, rather than attract, the sticky surface present on some disposable earplugs). The low surface energy material can be any material naturally exhibiting low surface energy or can be a material incorporated into a material of the wall surface 120 (e.g., the separator assembly 40, and thus the wall surface 120, can be a molded plastic, with the plastic material or resin including a low surface energy additive, such as a flouropolymer (e.g., available from 3M Company of St. Paul, Minn. under the trade name 3M™ Dyneon™)).

The optional anti-bonding constructions or features in accordance with the present disclosure include any surface feature that lessens frictional interface with an earplug as compared to the frictional interface that would otherwise be present between the earplug and a bore wall surface that did not include the anti-bonding construction or feature. The anti-bonding construction or feature can be chemical in nature (e.g., low surface energy material or coating), mechanical in nature (e.g., macroscopic roughness such as ribs), or a combination of both. In yet other embodiments, the wall surface 120 can be smooth and formed of a material not having a low surface energy attribute.

Figure 4C:
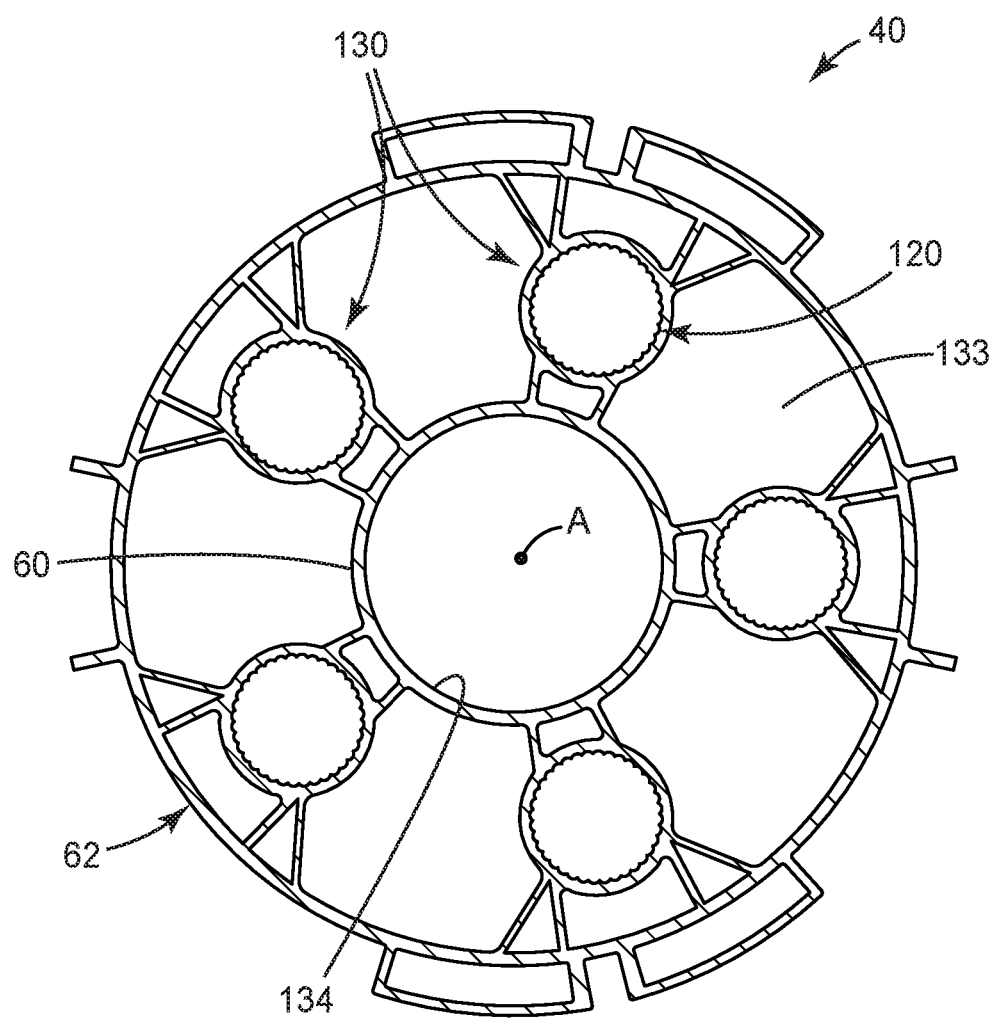
FIG. 4C is a cross-sectional view of the separator assembly of FIG. 4A, taken along the line 4C-4C.

In some embodiments the wall surfaces 120 are each supported or defined by a bracket or bore structure 130 extending between the inner and outer hubs 60, 62 as reflected by FIGS. 4A and 4C. The bracket structures 130 each support the corresponding wall surface 120 relative to the platform 52, with the corresponding bore 54 being open at a trailing end 132 of the bracket structure 130 (i.e., the exit opening 100 is defined at or by the trailing end 132 of the bracket structure 130). With this construction, an open region 133 is generated between circumferentially adjacent ones of the bracket structures 130. Alternatively, the separator assembly 40 can have a more solid construction (e.g., the bore structures 130 are formed as bores through a solid block of material). The trailing end 132, and thus the exit opening 100, can optionally be located slightly above the lower major face 102 defined by the outer hub 62 for reasons made clear below. Finally, the inner hub 60 optionally defines a passageway 134 for receiving a component of the index assembly 42 (FIG. 2A) as described below. In general terms, the passageway 134 is co-axial with the longitudinal axis A. In related embodiments, the inner hub 60, and thus the separator assembly 40, can be described as defining the longitudinal axis A along the passageway 134.

Returning to FIGS. 3A-4A, the separator assembly 40 optionally includes or provides various features for receiving the container 32 (FIG. 1A) and/or for mounting to the frame 28 (FIG. 1A). In some embodiments, for example, the separator assembly 40 includes or defines a capture ring 136 and a flange body 138.

The capture ring 136 is coaxially disposed about the outer hub 62 adjacent the upper edge 68. A slot 140 is defined between the capture ring 136 and the outer hub 62, and is sized to receive a neck (not shown) of the container 32 (FIG. 1A). In this regard, the separator assembly 40 can include various features, such as locking tabs 141, which selectively capture the container neck within the slot 140.

The flange body 138 includes a shoulder 142 and a flange 144. The shoulder 142 is connected to and extends from the capture ring 136, with the flange 144 projecting radially outwardly from the shoulder 142. In general terms, the flange body 138 is sized and shaped in accordance with features associated with the frame 28 (FIG. 1A) such that the separator assembly 40 can be mounted to the frame 28 via the flange body 138. In some embodiments the separator assembly 40 is desirably mounted to the frame 28 such that the separator assembly 40 cannot rotate relative to the frame 28. The flange body 138 can include or provide additional features useful in ensuring this non-rotational coupling with the frame 28, such as pins 146a, 146b arranged adjacent a corresponding notch 148a, 148b in the flange 144.

Returning to FIGS. 2A and 2B, the index assembly 42 includes a handle 150, a plate 152, a mixing body 154, and optionally a shield 156. In general terms, the plate 152 defines a dispensing aperture 160, and is connected to the handle 150, as are the mixing body 154 and the shield 156. The handle 150, in turn, is rotatably coupled to the separator assembly 40. With rotation of the handle 150 about the longitudinal axis A, the dispensing aperture 160 is brought into alignment with individual ones of the bores 54 to release an earplug (not shown) from the bore 54. The mixing body 154 and the shield 156 (where provided) also rotate with the handle 150, effectuating mixing of the grouping of earplugs within the well 56.

Figure 6:
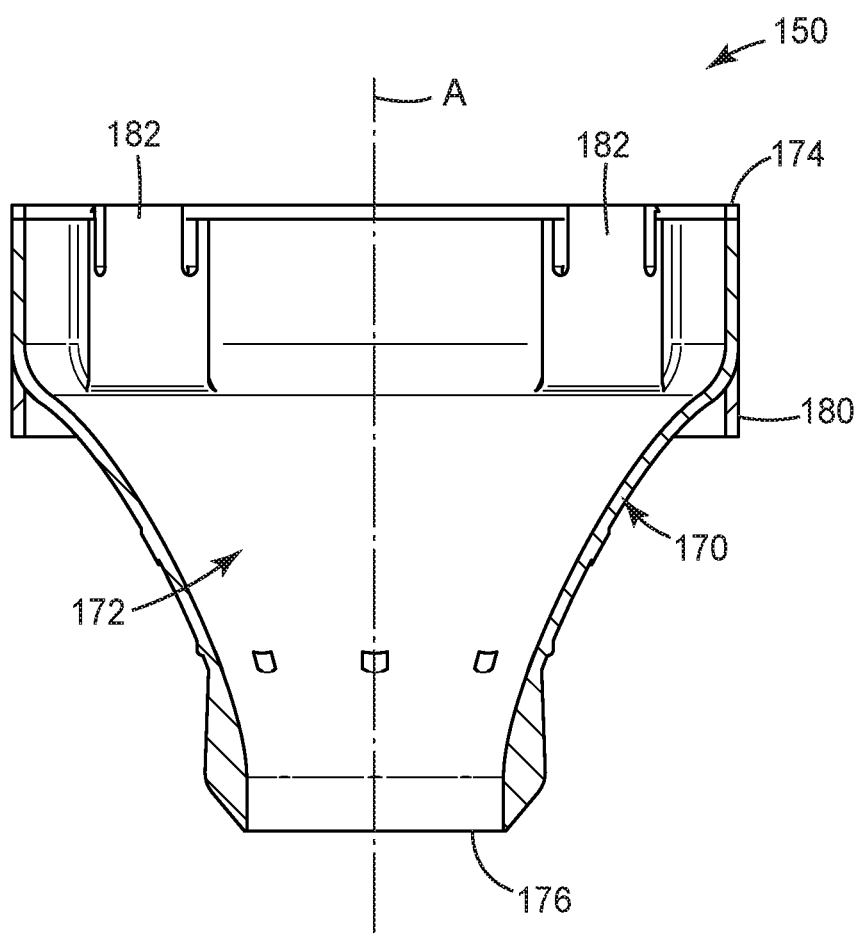
FIG. 6 is a cross-sectional view of a handle portion useful with the index assembly of FIG. 2A.

With additional reference to FIG. 6, the handle 150 is a hollow body in some embodiments, including a side wall 170 defining a chamber 172. The handle 150 is open to the chamber 172 at an upper end 174 and a dispensing end 176. The handle 150 can have various shapes and sizes, and in some configurations is symmetric about the longitudinal axis A (e.g., in some embodiments, the handle 150 can be viewed as defining the longitudinal axis A). Further, the handle 150 can have a generally tapering diameter in a direction of the dispensing end 176 (e.g., a funnel shape). As made clear below, individual earplugs (not shown) are dispensed to a user from the dispensing end 176, with the optional tapered or funnel shape of the handle 150 establishing a reduced diameter at the dispensing end 176 conducive to placement of a user's hand (and thus more accurate, funneled dispensing of an earplug into the user's palm). The handle 150 can further include features that promote rotation of the handle 150 by a user's hand, such as optional finger grips 178.

The handle 150 includes or forms one or more features that facilitate assembly with complimentary features the plate 152. For example, the side wall 170 forms a sleeve 180 at the upper end 174 and having an outer diameter commensurate with (e.g. slightly smaller than) an inner diameter of the outer hub 62 (FIG. 4A) of the separator assembly 40. One or more tabs 182 are formed radially inward (relative to the longitudinal axis A) of the sleeve 180 at the upper end 174. The tab(s) 182 is configured for mounting with a corresponding feature of the plate 152 as described below. A wide variety of other mounting configurations are also acceptable. For example, while in some embodiments the handle 150 is indirectly coupled to the separator assembly 40 via the plate 152 (and the mixing body 154), in other embodiments, the handle 150 can be more directly rotatably mounted to the separator assembly 40.

With specific reference to FIG. 2A, the plate 152 has a circular-shaped perimeter, and forms the dispensing aperture 160. A size and shape of the dispensing aperture 160 generally corresponds with a size (e.g., diameter) of the exit opening 100 (FIG. 4A) of each of the bores 54 (e.g., a cross-sectional area of the dispensing aperture 160 is slightly larger than a cross-sectional area of each of the exit openings 100). Further, a radial location (relative to the longitudinal axis A (FIG. 2B)) of the dispensing aperture 160 corresponds with a radial location (relative to the longitudinal axis A) of each of the bores 54 such that upon final assembly of the dispensing unit 22 (FIG. 1A), the dispensing aperture 160 can be longitudinally aligned with respective ones of the exit openings 100.

As mentioned above, the plate 152 includes or forms various features that promote assembly with the handle 150 in some embodiments. For example, the plate 152 can form one or more slots 190 sized to receive a corresponding one of the tabs 182 associated with the handle 150. Other mounting configurations are equally acceptable. In some constructions of the present disclosure, however, the handle 150 and the plate 152 are configured to be rigidly coupled to one another (e.g., upon final assembly, the plate 152 rotates with rotation of the handle 150).

In addition, the plate 152 optionally includes features configured for coupling with complimentary features provided with the mixing body 154. For example, the plate 152 can form one or more channels 192 configured for mounting with a corresponding feature of the mixing body 154 as described below. A wide variety of other mounting configurations are also acceptable.

The mixing body 154 is shown in greater detail in FIGS. 7A-7D, and includes or forms a mixing region 200 and a base 202. The mixing region 200 is sized and shaped to interface with earplugs (not shown) and other components of the dispensing unit 22 (FIG. 1A) as described in greater detail below. The base 202 extends from the mixing region 200, and is configured for mounted assembly with the plate 152 (FIG. 2A) and the separator assembly 40 (FIG. 2A).

Figure 7A:
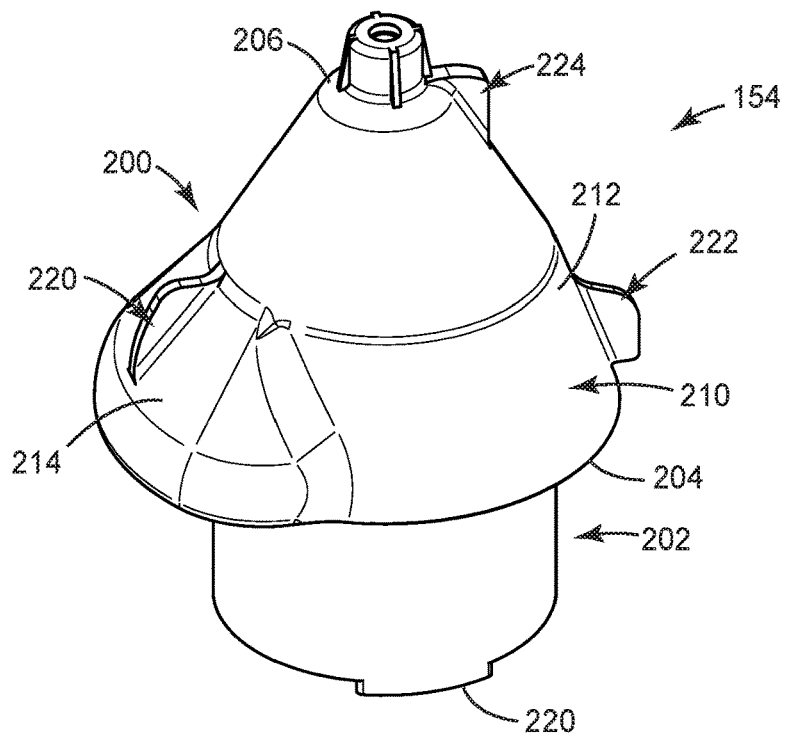
FIG. 7A is a top perspective view of a mixing body useful with the index assembly of FIG. 2A.
Figure 7B:
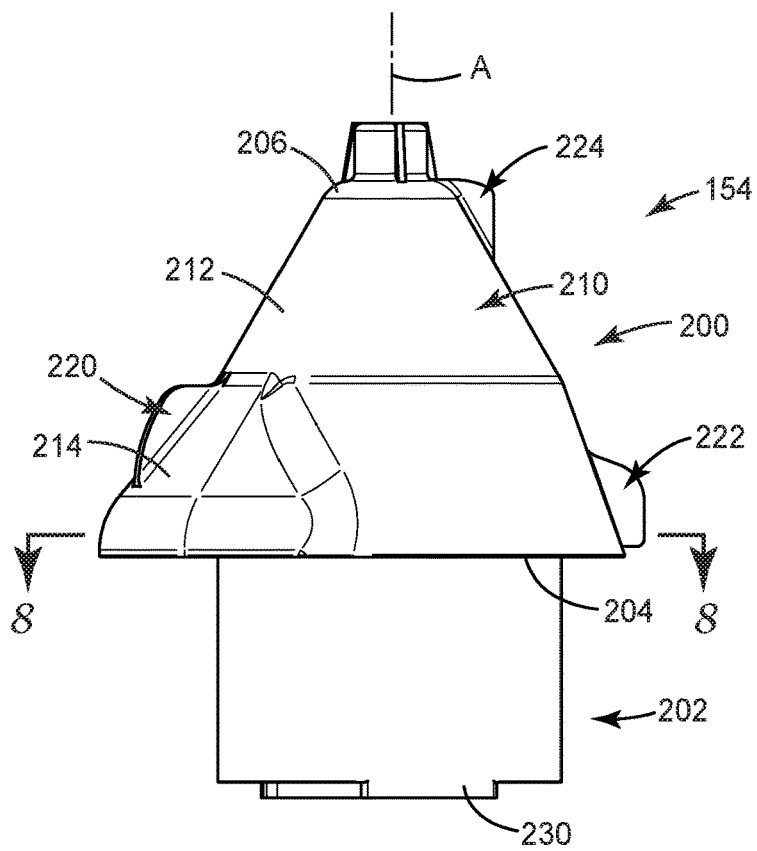
FIG. 7B is a side view of the mixing body of FIG. 7A.
Figure 7C:
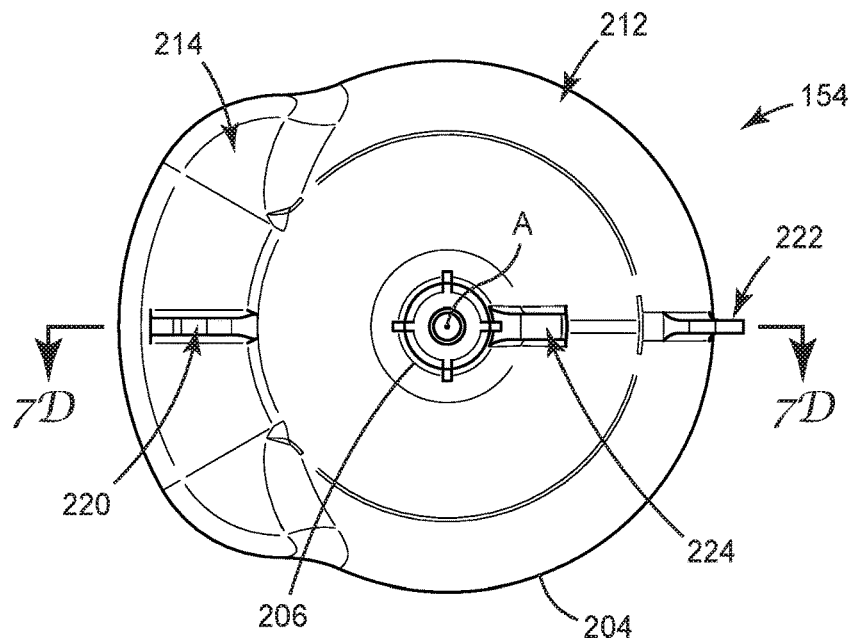
FIG. 7C is a top plan view of the mixing body of FIG. 7A.
Figure 7D:
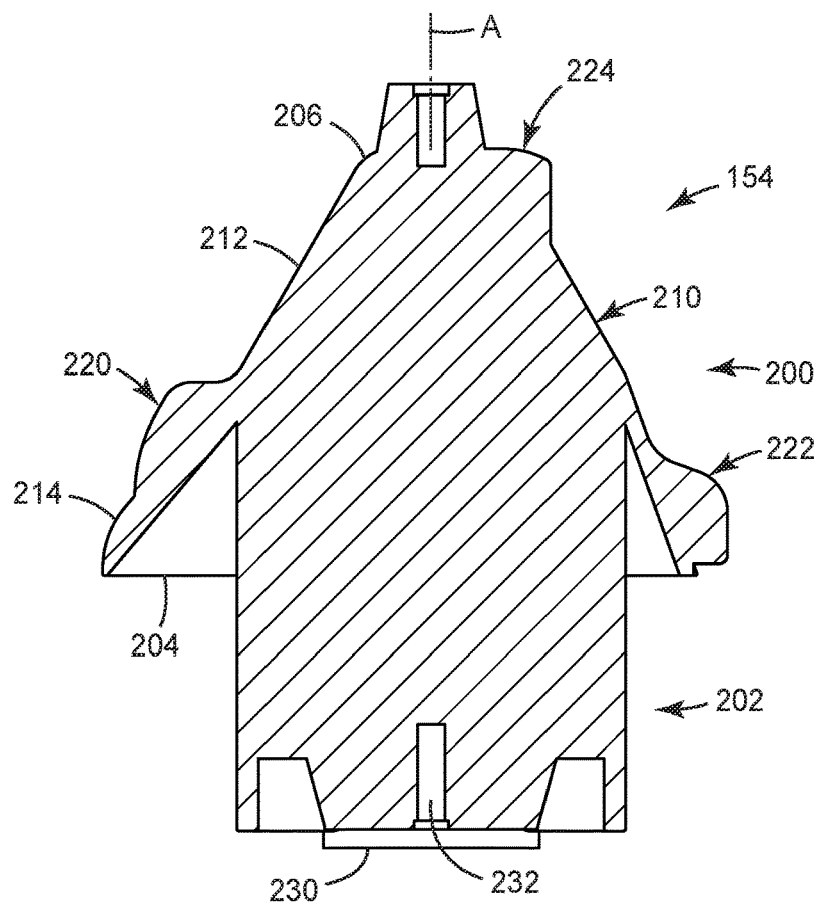
FIG. 7D is a cross-sectional view of the mixing body of FIG. 7C, taken along the line 7D-7D.

The mixing region 200 extends in the longitudinal direction between a lower end 204 and an upper end 206. The mixing region 200 can be radially spaced from the base 202 adjacent the lower end 204, or the mixing body 154 can have a more solid construction. Regardless, an exterior surface 210 of the mixing body 154 along the mixing region 200 generally tapers in outer dimension (e.g., outer diameter) from the lower end 204 to the upper end 206. More particularly, the exterior surface 210 is defined by or along a cone portion 212 and a paddle portion 214. The cone portion 212 is generally conical in shape, tapering in outer diameter from the lower end 204 to the upper end 206. As best reflected in by FIG. 7C, the paddle portion 214 projects radially outward (relative to the longitudinal axis A) from the cone portion 212 at or immediately adjacent the lower end 204. The paddle portion 214 thus renders the exterior surface 210 to have an asymmetrical shape. For example, FIG. 7D is a cross-sectional illustration of the mixing body 154 in a plane that includes the longitudinal axis A and passes through the paddle portion 214. As shown, the exterior surface 210 is asymmetrical relative to the longitudinal axis A.

Figure 8:
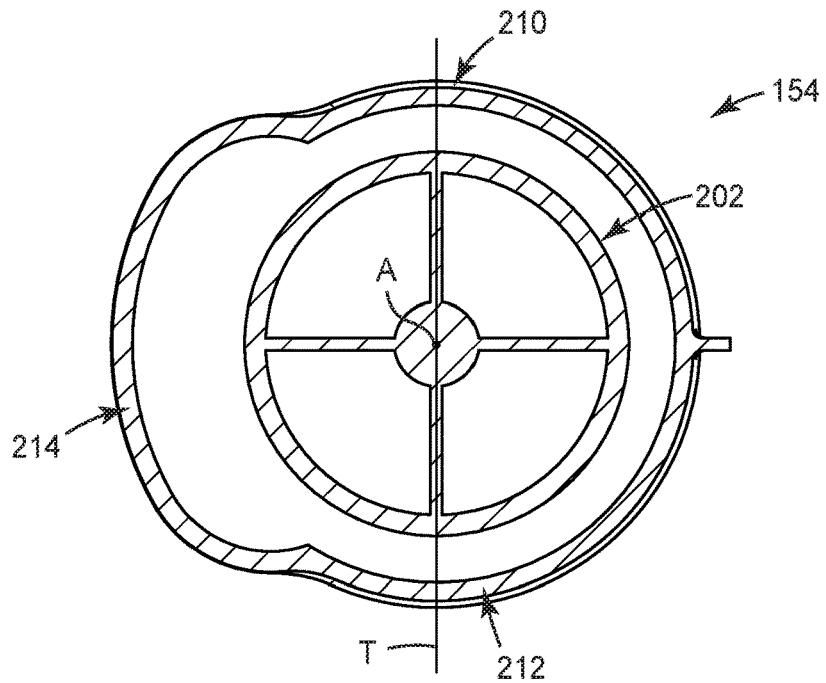
FIG. 8 is a cross-sectional view of the mixing body of FIG. 7B, taken along the line 8-8.

The asymmetrical shape of the exterior surface 210, as generated by the cone portion 212 and the paddle portion 214, can alternatively be described with reference to the paddle portion 214 representing an outward deviation from an otherwise continuous, uniform shape of the cone portion 212. For example, FIG. 8 reflects that the exterior surface 210 along the cone portion 212 has a substantially uniform curvature in a plane perpendicular to the longitudinal axis A. A shape of the exterior surface 210 in a plane perpendicular to the longitudinal axis A can have a substantially uniform or constant radius (e.g., within 5% of a truly uniform radius) along the cone portion 212. In this same plane, the exterior surface 210 has an increased radius (relative to the longitudinal axis A) along the paddle portion 214 (as compared to the cone portion 212). Thus, in a plane perpendicular to the longitudinal axis A and passing through the paddle portion 214 (e.g., the plane of FIG. 8), the exterior surface 210 is asymmetrical relative to a hypothetical transverse line T that is in the plane, intersects the longitudinal axis A, and is off-set from the paddle portion 214.

Figure 9:
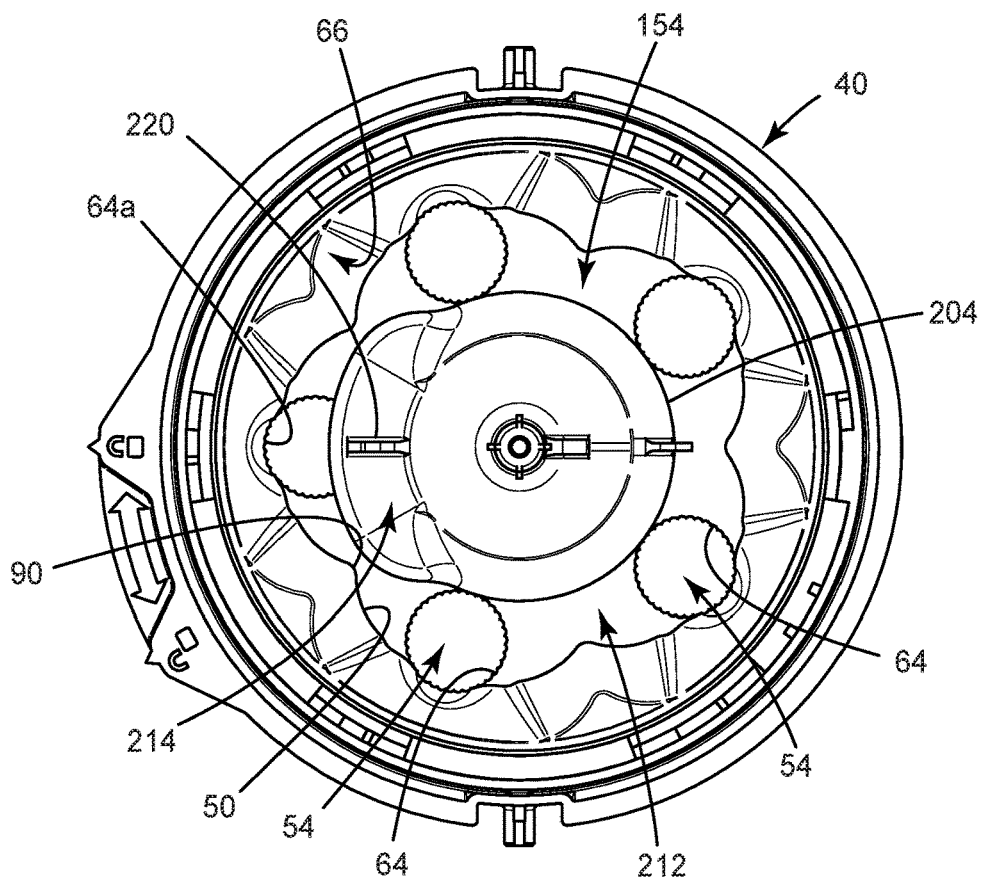
FIG. 9 is a top plan view of the mixing body of FIG. 7A mounted to the separator assembly of FIG. 3A.

Returning to FIGS. 7A-7D, geometries of the exterior surface 210 at the lower end 204 are selected in accordance with geometries of the bores 54 (FIG. 2A) relative to the longitudinal axis A. In general terms, the mixing body 154 and the separator assembly 40 (FIG. 2A) are collectively sized and shaped such that upon final assembly, the lower end 204 selectively covers a segment of one (or more) of the bores 54 along the paddle portion 214 whereas a remainder of the bores 54 are not covered by the lower end 204 along the cone portion 212. For example, FIG. 9 illustrates the mixing body 154 upon final mounting to the separator assembly 40, located immediately at or adjacent the platform 52. A radius (relative to the longitudinal axis A) of the lower end 204 along the cone portion 212 approximates or is slightly less than the interior radius (relative to the longitudinal axis A) collectively defined by the circumferentially arranged entrance openings 64 of the bores 54. Thus, the lower end 204 does not "cover" any region or segment of the entrance openings 64 along the cone portion 212, and earplugs (not shown) can freely enter the entrance openings 64 otherwise aligned with the cone portion 212. Conversely, a radius (relative to the longitudinal axis) A of the lower end 204 along the paddle portion 214 is greater than the interior radius collectively defined by the circumferentially arranged entrance openings. As such, the lower end 204 can "cover" a segment of at least one of the entrance openings 64 along the paddle portion 214 as the paddle portion 214 is brought or rotated into alignment with the corresponding entrance opening 64 (e.g., the entrance opening 64a in the arrangement of FIG. 9), and earplugs are prevented from freely entering the so-covered entrance opening 64. The paddle portion 214 can be dimensioned to selectively cover only a segment of an entrance opening 64 as shown (due, in part, to possible interference with the guide face 66 were the paddle portion 214 dimensioned to cover an entirety of an entrance opening 64) as shown; alternatively, the paddle portion 214 can be configured to selectively cover an entirety of one or more of the entrance openings 64. An arc length of the paddle portion 214 at the lower end 204 can approximate (e.g., be slightly greater than) a circumferential distance between immediately adjacent ones of the entrance openings 64, and can be on the order of the circumferential distance between adjacent entrance openings 64. Other geometries appropriate for selectively "covering" at least a segment of at least one entrance opening 64 are also acceptable (e.g., the paddle portion 214 at the lower end 204 can have dimensions that are greater or lesser than those reflected by FIG. 9) so long as at least one of the entrance openings 64 is "uncovered".

Returning to FIGS. 7A-7D, the mixing body 154 optionally includes one or more additional features that promote mixing of earplugs (not shown). For example, a first blade 220 can be formed as a projection from the exterior surface 210 along the paddle portion 214. The first blade 220 is arranged radially relative to the longitudinal axis A, and can be off-set from the lower end 204. A second blade 222 can also be formed as a projection from the exterior surface 210 along the cone portion 212, for example diametrically opposite the first blade 220. The second blade 222, where provided, can be off-set from the lower end 204, but optionally is more proximate the lower end 204 than the first blade 220. The first and second blades 220, 222 represent outward projections from the otherwise smooth exterior surface 210, and are configured to promote mixing of earplugs that are otherwise loosely arranged about the mixing body 154 with rotation of the index assembly 42 (FIG. 2A). The mixing body 154 can optionally include or form a third blade 224 adjacent the upper end 206 for reasons made clear below. The blades 220-224 can assume other configurations that may or may not be implicated by the FIGURES, and in other embodiments, one or more (including all) of the blades 220-224 can be omitted.

The base 202 can assume various forms appropriate for mounting to the separator assembly 40. In some embodiments, the base 202 is cylindrically-shaped, sized to be rotationally received within the passageway 134 (FIG. 4A) of the separator assembly 40. The base 202 can further be configured for coupling with the plate 152 (FIG. 2A). For example, the base 202 forms one or more fingers 230 each sized to be frictionally received within a corresponding one of the channels 192 (FIG. 2A) in the plate 152, as well as an interiorly threaded bore 232 for receiving a screw or other fastening member (that is also connected to the plate 152). Other mounting configurations are equally acceptable. In yet other embodiments, the base 202 can be configured for direct coupling to the handle 150 (FIG. 2A).

Figure 10A:
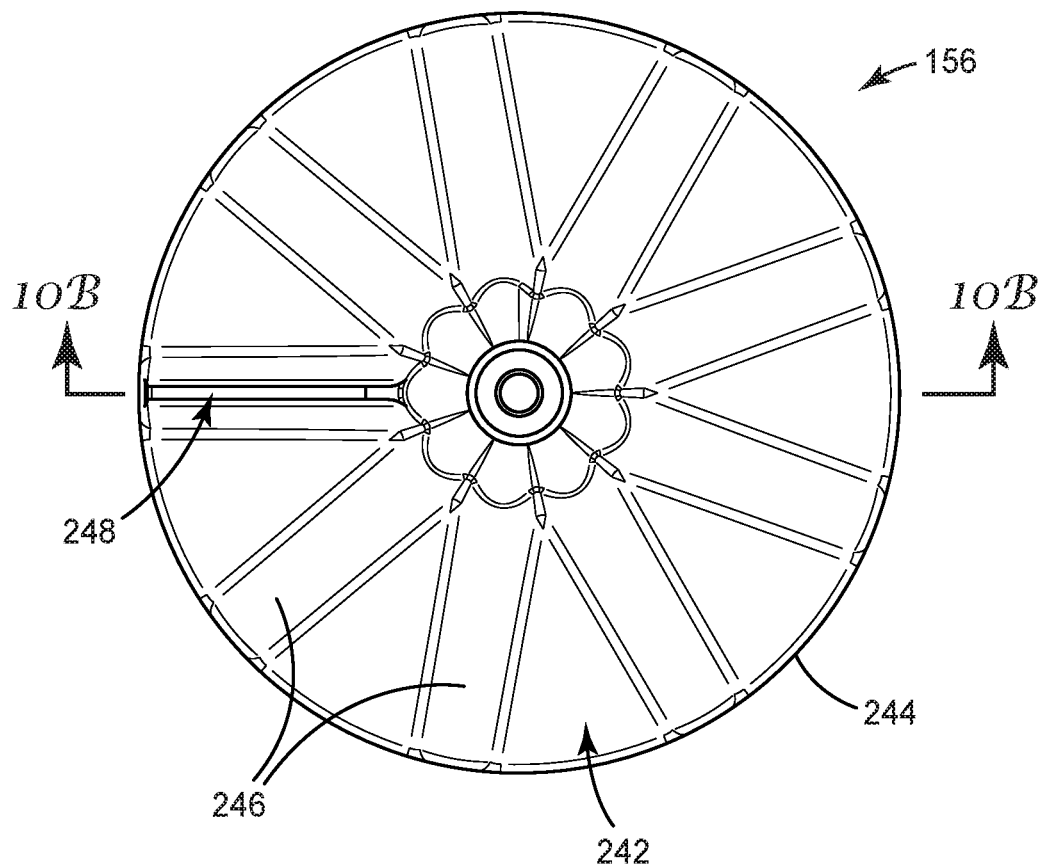
FIG. 10A is a top plan view of a shield useful with the index assembly of FIG. 2A.
Figure 10B:
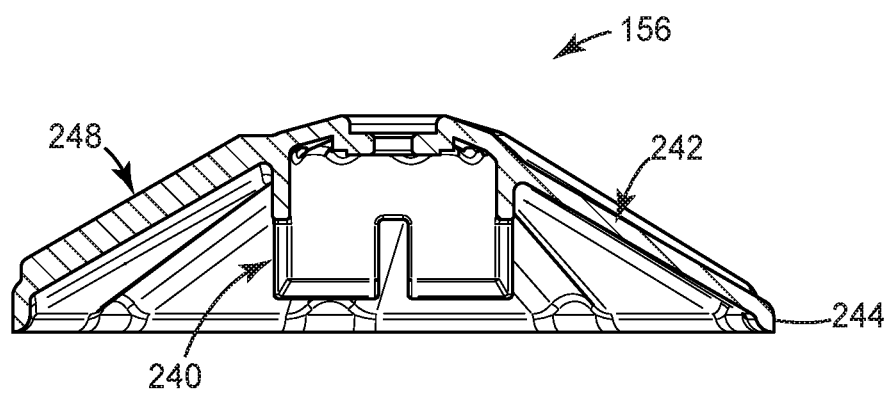
FIG. 10B is a cross-sectional view of the shield of FIG. 10A, taken along the line 10B-10B.

Returning to FIG. 2A, where provided, the shield 156 is configured for assembly to the mixing body 154, and in other embodiments can be integrally formed with the mixing body 154. Regardless, and with reference to FIGS. 10A and 10B, the shield 156 includes or defines a base 240 and a shield wall 242. The shield wall 242 projects radially outwardly from the base 240 to a perimeter edge 244. Further, the shield wall 242 defines a conical-like shape, such that the shield 156 is akin to an umbrella. Contours 246 (e.g., grooves or slots) can be formed in an outer surface of the shield wall 242 for reasons made clear below. Regardless, an outer diameter of the shield 156 at the perimeter edge 244 is sized in accordance with corresponding features of the mixing body 154 and the well 56 (FIG. 4A) as described below. In some embodiments, the shield 156 can further include or form one or more mixing blades 248.

Figure 11A:
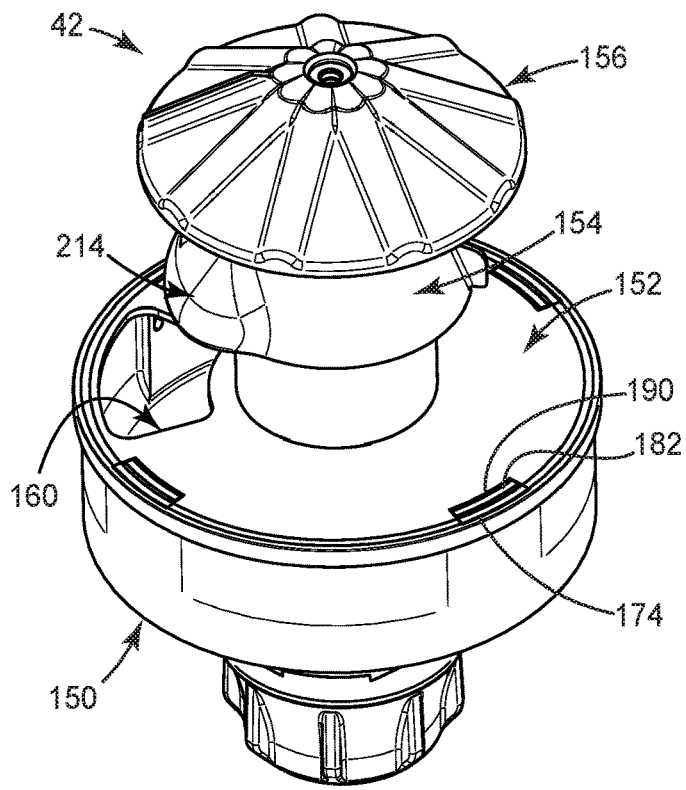
FIG. 11A is a perspective view of the index assembly of FIG. 2A.
Figure 11B:
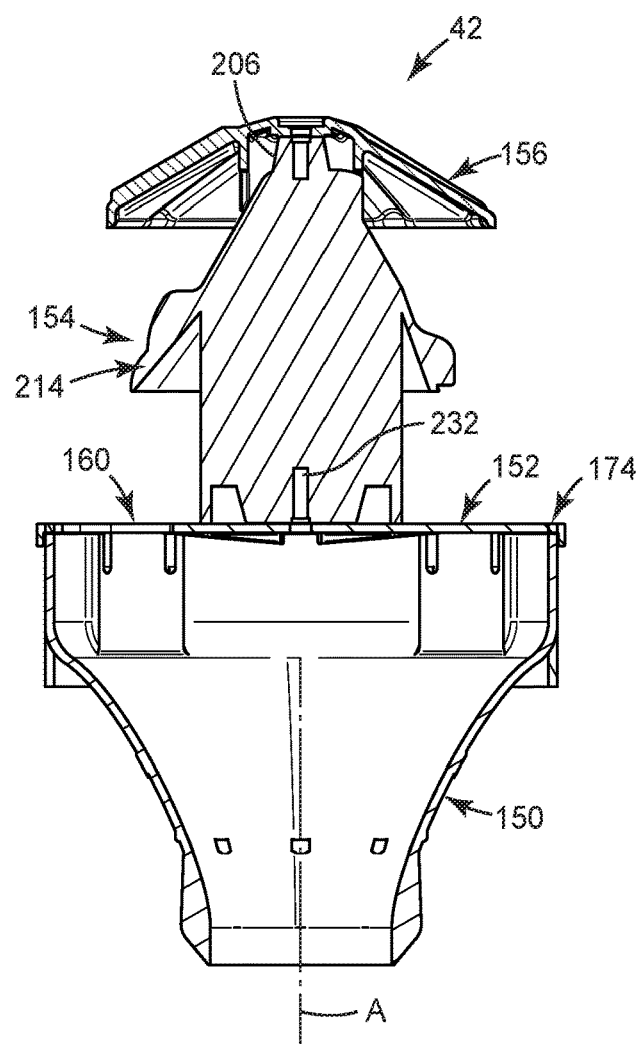
FIG. 11B is a cross-sectional view of the index assembly of FIG. 11A.

Final construction of the index assembly 42 is shown in FIGS. 11A and 11B. The plate 152 is rigidly coupled to the upper end 174 of the handle 150, for example via insertion of the tabs 182 within corresponding ones of the slots 190. Other assembly configurations are also envisioned, appropriate for effectuating a rotational lock or rigid coupling between the handle 150 and the plate 152 (i.e., the plate 152 rotates with rotation of the handle 150). The mixing body 154 is also rigidly coupled to the plate 152, for example via insertion of the mixing body fingers 230 (FIG. 7A) within corresponding ones of the plate channels 192 (FIG. 2A). Rigid attachment between the plate 152 and the mixing body 154 can be further enhanced by a fastening device (not shown), such as a screw, attached to the plate 152 and the threaded bore 232 of the mixing body 154. Other assembly configurations are also envisioned, appropriate for effectuating a rotational lock or rigid coupling between the mixing body 154 and the plate 152 (and thus between the mixing body 154 and the handle 150) such that the mixing body 154 rotates with rotation of the handle 150. The shield 156, where provided, is rigidly coupled to the upper end 206 of the mixing body 154. Upon final assembly, the mixing body 154 is spatially arranged relative to the plate 152 such that the paddle portion 214 is longitudinally aligned with the dispensing aperture 160 (i.e., relative to the longitudinal axis A, the lower end 204 of the mixing body 154 extends radially "over" a portion of the dispensing aperture 160 at the paddle portion 214). Due to the rotationally locked construction of the index assembly 42, longitudinal alignment of the paddle portion 214 with the dispensing aperture 160 remains intact with rotation of the handle 150 about the longitudinal axis A.

Figure 12A:
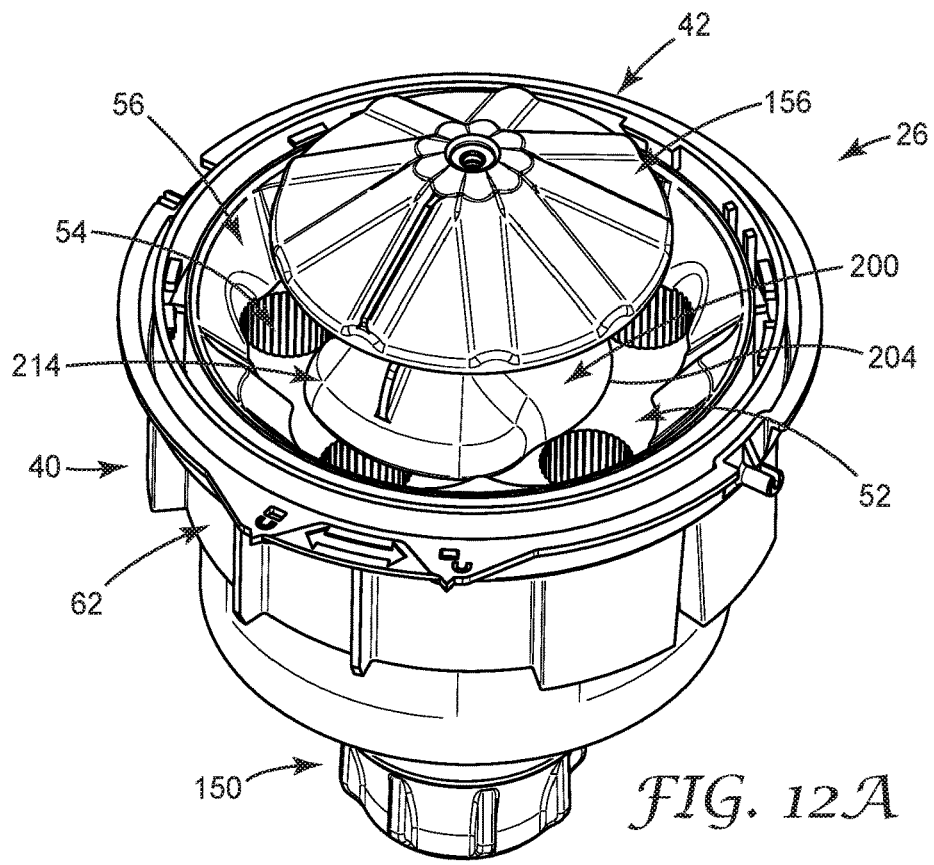
FIG. 12A is a perspective view of the dispensing mechanism of FIG. 2A upon final assembly.
Figure 12B:
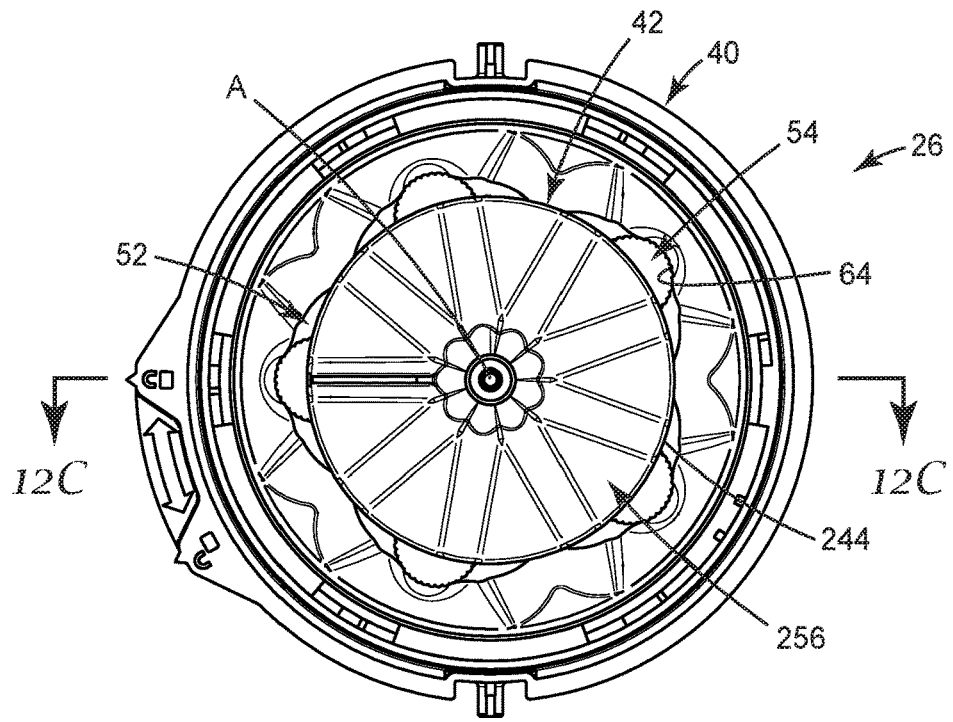
FIG. 12B is a top plan view of the dispensing mechanism of FIG. 12A.
Figure 12C:
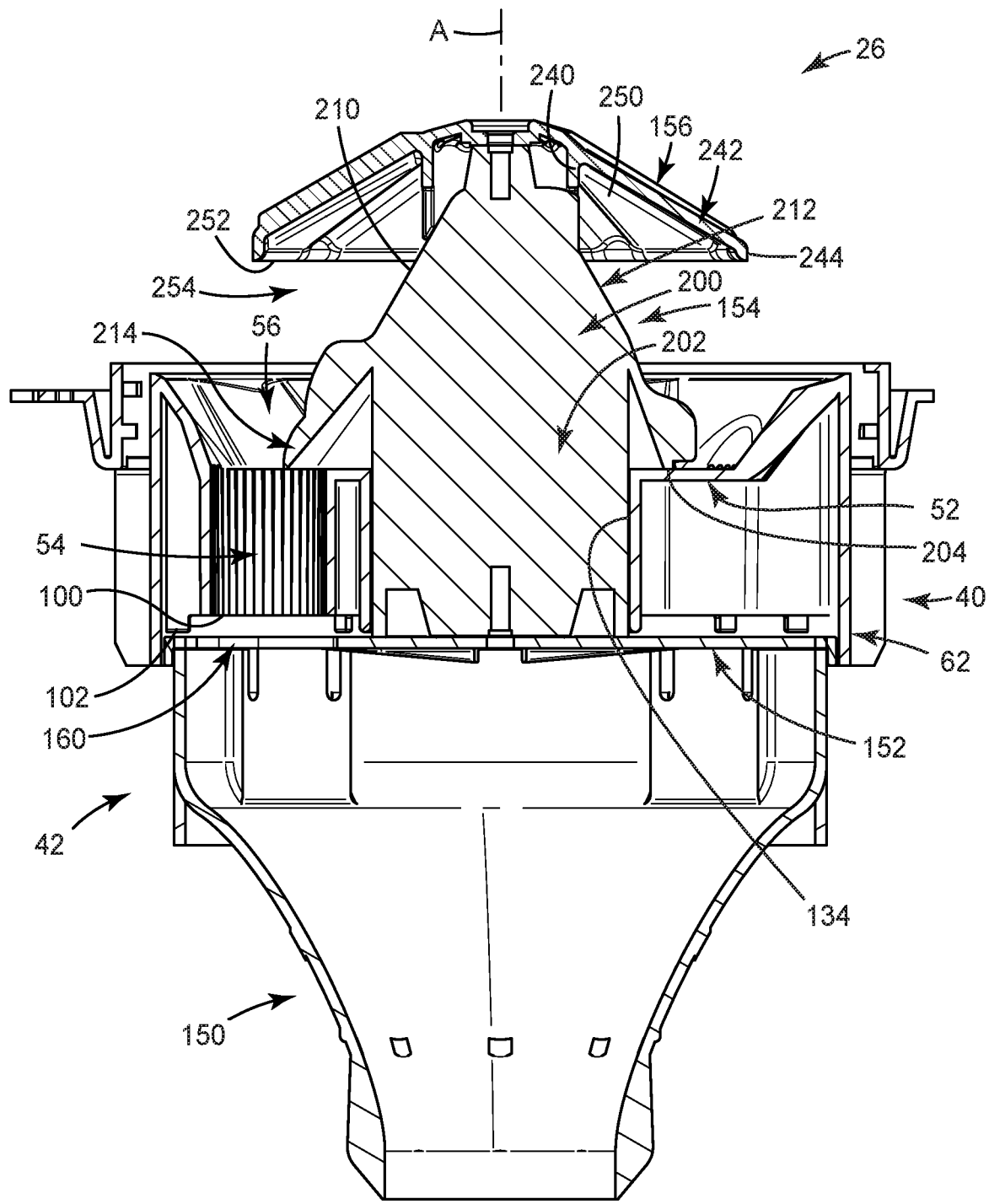
FIG. 12C is a cross-sectional view of the dispensing mechanism of FIG. 12B, taken along the line 12C-12C.

Final construction of the dispensing mechanism 26 is shown in FIGS. 12A-12C. The index assembly 42 is rotatably coupled to the separator assembly 40 (such that the index assembly 42 can rotate relative to the separator assembly 40 about the longitudinal axis A). For example, the base 202 of the mixing body 154 is rotatably received within the passageway 134 of the separator assembly 40, locating the mixing region 200 "above" (relative to the orientations of the views) the platform 52. The plate 152, in turn, is captured within the outer hub 62 of the separator assembly 40, at or slightly below the lower major face 102. It will be recalled that the plate 152 is coupled to the mixing body 154. This attachment can thus retain the plate 152 relative to the separator assembly 40 (e.g., in the upright orientation of the views, the lower end 204 of the mixing region 200 can contact or bear against the platform 52 due to gravity; a longitudinal distance between the lower end 204 and the plate 152 corresponds with (e.g., is slightly greater than) a longitudinal distance between the platform 52 and the lower major face 102, thus maintaining the plate 152 as shown). Nesting of the plate 152 (and/or the handle 150) within the outer hub 62 is such that the outer hub 62 does not overtly impede rotation of the index assembly 42 (e.g., frictional interface between the plate 152 and the outer hub 62, if any, is minimal). Regardless, the lower end 204 of the mixing region 200 is located within the well 56 of the separator assembly 40, and the dispensing aperture 160 can be brought into selective alignment with the exit opening 100 of individual ones of the bores 54 with rotation of the index assembly 42. The paddle portion 214 remains aligned with the dispensing aperture 160 upon rotation of the index assembly 42 such that the paddle portion 214 partially covers and the dispensing aperture 160 is aligned with the same individual one of the bores 54 as the index assembly 42 is rotated.

Where provided, the shield 156 is located outside of (or above) the well 56. As shown in FIG. 12C, the base 240 is mounted above the upper end 206 of the mixing body 154, with the shield wall 242 extending outwardly as well as downwardly toward the platform 52. A taper angle of the shield wall 242 differs from that of the cone portion 212 such that the shield wall 242 is radially spaced from the exterior surface 210 of the mixing region 200. A spacing 250 is created between the exterior surface 210 and an underside 252 of the shield wall 242. With this arrangement, the perimeter edge 244 is radially spaced from the mixing body 154. The perimeter edge 244 is longitudinally spaced from the platform 52, thereby establishing a chamber 254 between the shield 156 and the platform 52 (with the chamber 254 including the well 56). As described below, earplugs (not shown) can be loosely disposed within the chamber 254, with the shield 156 isolating the earplugs within the chamber 254 from other earplugs located above the shield 156. In this regard, and as best reflected in FIG. 12B, an outer diameter of the shield 156 at the perimeter edge 244 is greater than an interior diameter collectively defined by the entrance openings 64 of the bores 54. Stated otherwise, in the final assembled state of FIGS. 12A-12C, the shield 156 projects over at least a portion of each of the bores 54, better ensuring that the chamber 254 includes at least a portion of each of the bores 54.

Figure 13A:
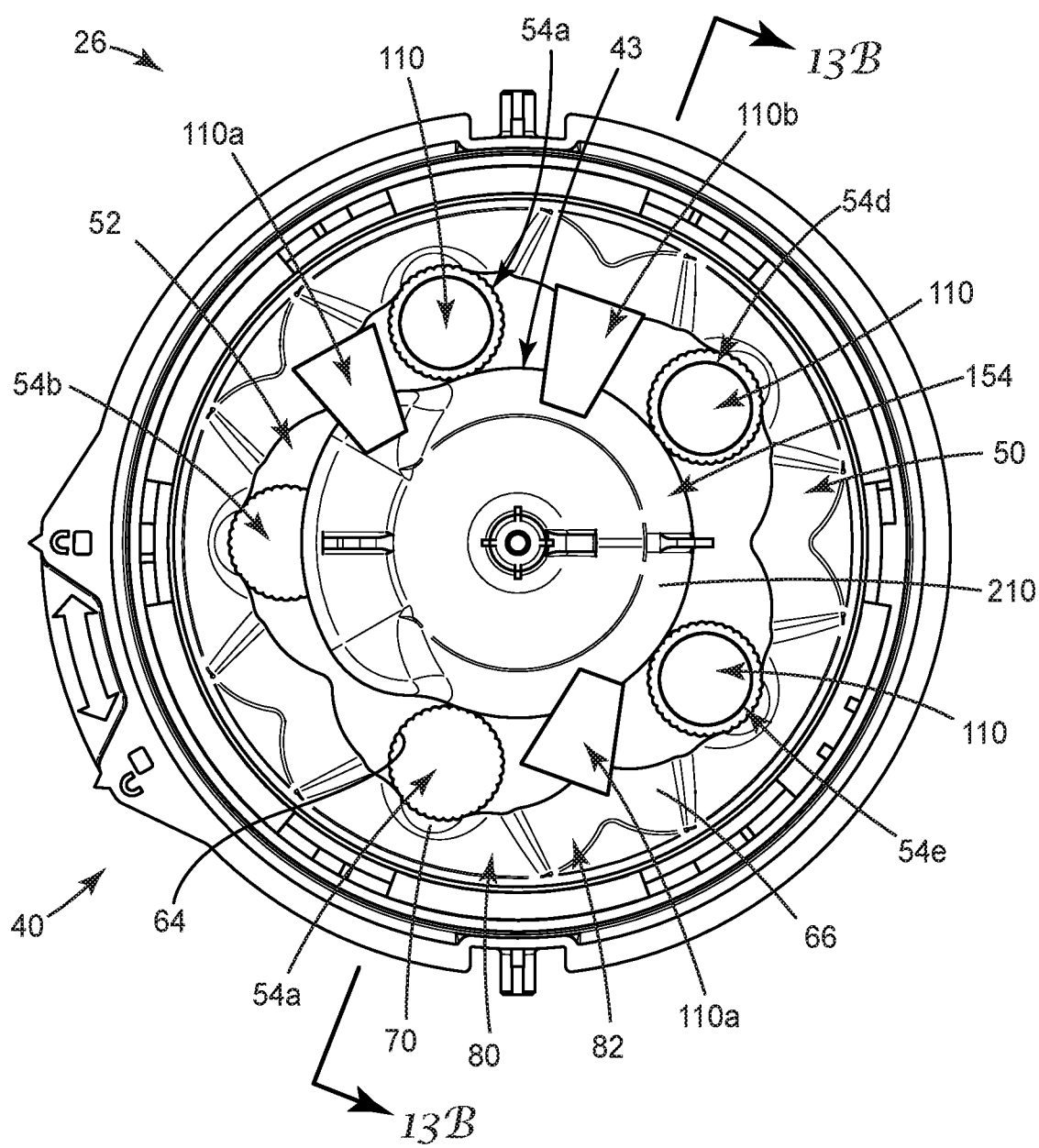
FIGS. 13A-13D illustrate operation of the dispensing mechanism of FIG. 2A in handling disposable earplugs prior to dispensing the earplugs.
Figure 13B:
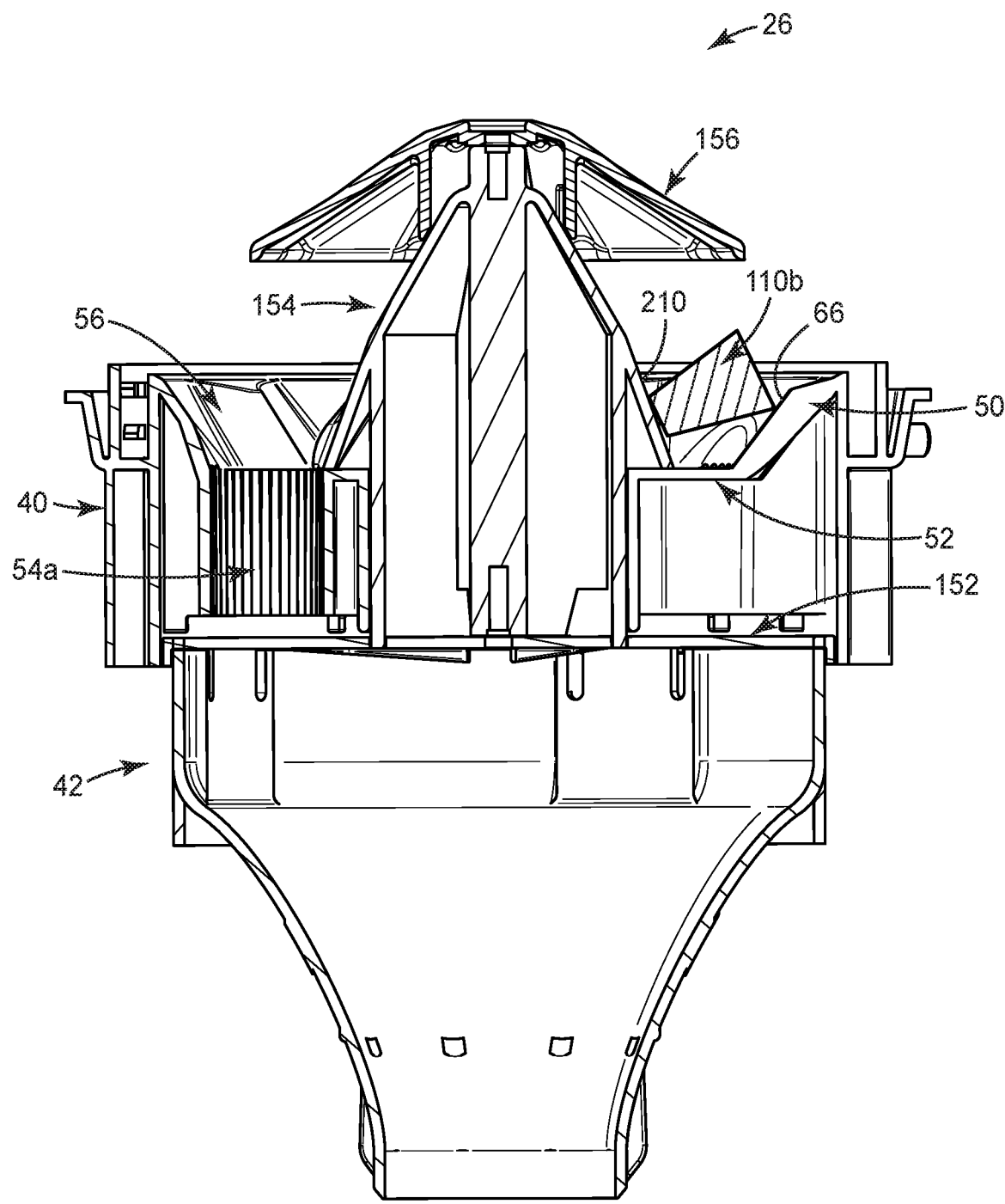

Operation of the dispensing mechanism 26 in handling disposable earplugs 110 for subsequent dispensing is generally reflected in FIGS. 13A-13D. For ease of illustration and understanding, the optional shield 156 is removed from the view of FIG. 13A. In the operational state of FIG. 13A, first and second bores 54a, 54b are empty, whereas each of the third-fifth bores 54c-54e is loaded with an earplug 110 (as a point of reference, the arrangement of FIG. 13A can be representative of a scenario in which an earplug has just been dispensed from the second bore 54b). Several additional earplugs 110a-110c are loosely or randomly arranged within the well 56 in a vicinity of the platform 52. It will be understood that un-loaded earplugs will naturally and randomly assume virtually any orientation, and any un-loaded earplugs proximate the well 56 will randomly contact the dispensing mechanism 26 at any available surface such that the arrangements of FIG. 13A are merely one example. In some embodiments, a spacing between and geometry of the mixing body 154 and the guide wall 50 encourages at least some of the un-loaded earplugs 110a-110c slightly away from the platform 52 and into an orientation conducive to subsequent self-loading into an open bore 54. For example, FIG. 13B illustrates one possible, naturally occurring orientation of the second un-loaded earplug 110b. With cross-reference between FIGS. 13A and 13B, a radial distance between the guide face 66 of the guide wall 50 and the exterior surface 210 of the mixing body 154 is less than a length of the earplug 110b such that when arranged in the orientation of FIGS. 13A and 13B, the earplug 110b is lifted slightly above the platform 52. Further, the opposing taper angles of the guide wall 50 and the mixing body 154 tilts the earplug 110b (i.e., a centerline of the earplug 110b is non-parallel with the plane of the platform 52), with this tilted orientation being conducive to the earplug 110b self-loading within an open one of the bores 54 once aligned as described below. It will be understood that the location and orientation of the second earplug 110b in FIGS. 13A and 13B is only one possibility, and in many instances, un-loaded earplugs can and will be in contact with the platform 52. Further, other disposable earplugs useful with the present disclosure can have a shorter length and thus may not span across the guide wall 50 and the mixing body 154 even in the orientation of FIG. 13B. By optionally lifting at least some of the un-loaded earplugs 110a-110c away from the platform 52, the likelihood of a stray, un-loaded earplug becoming lodged within gaps between moving parts of the dispensing mechanism 26 is reduced, thus minimizing malfunctions or "jamming" of the dispensing mechanism 26.

Figure 13C:
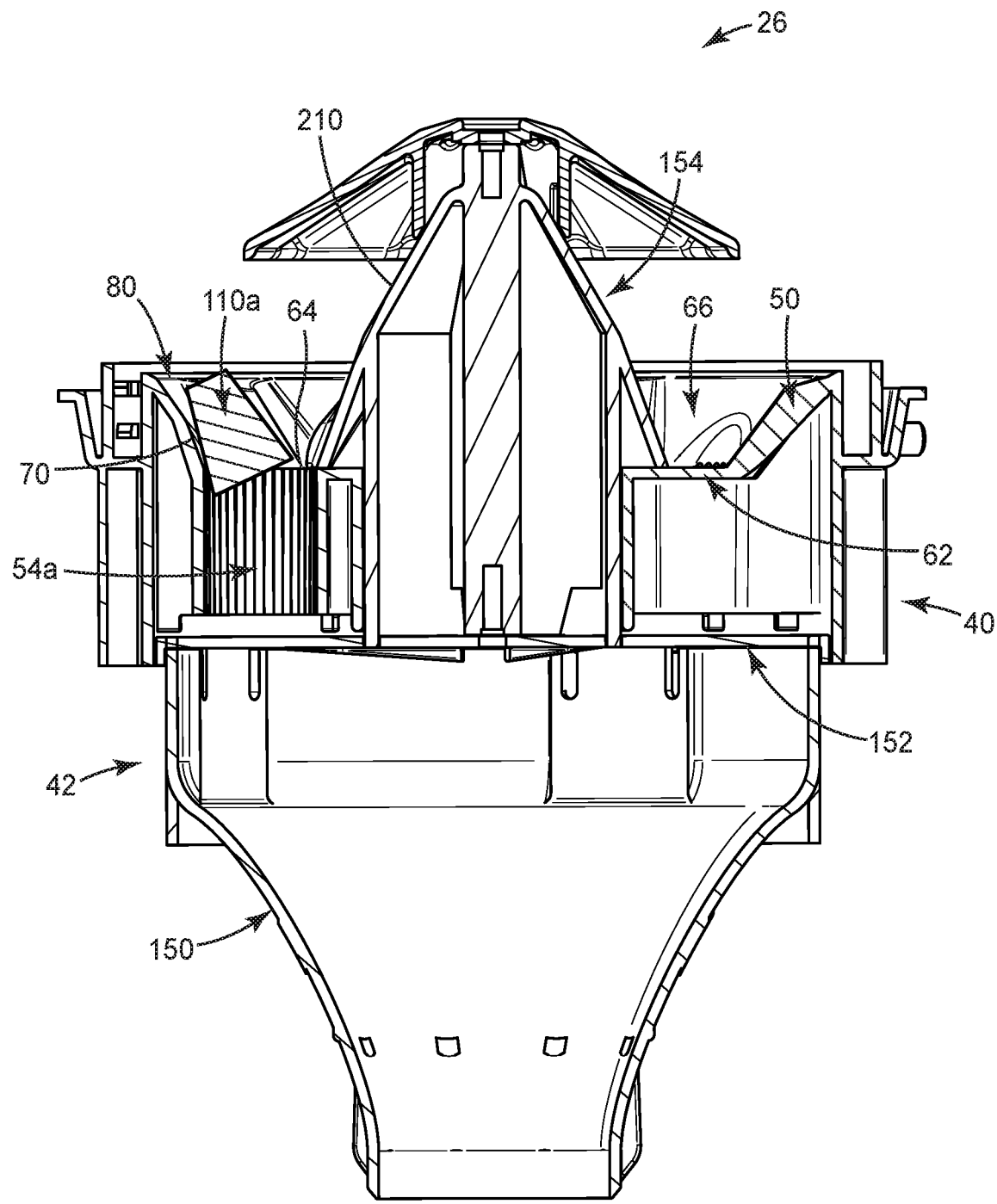
Figure 13D:
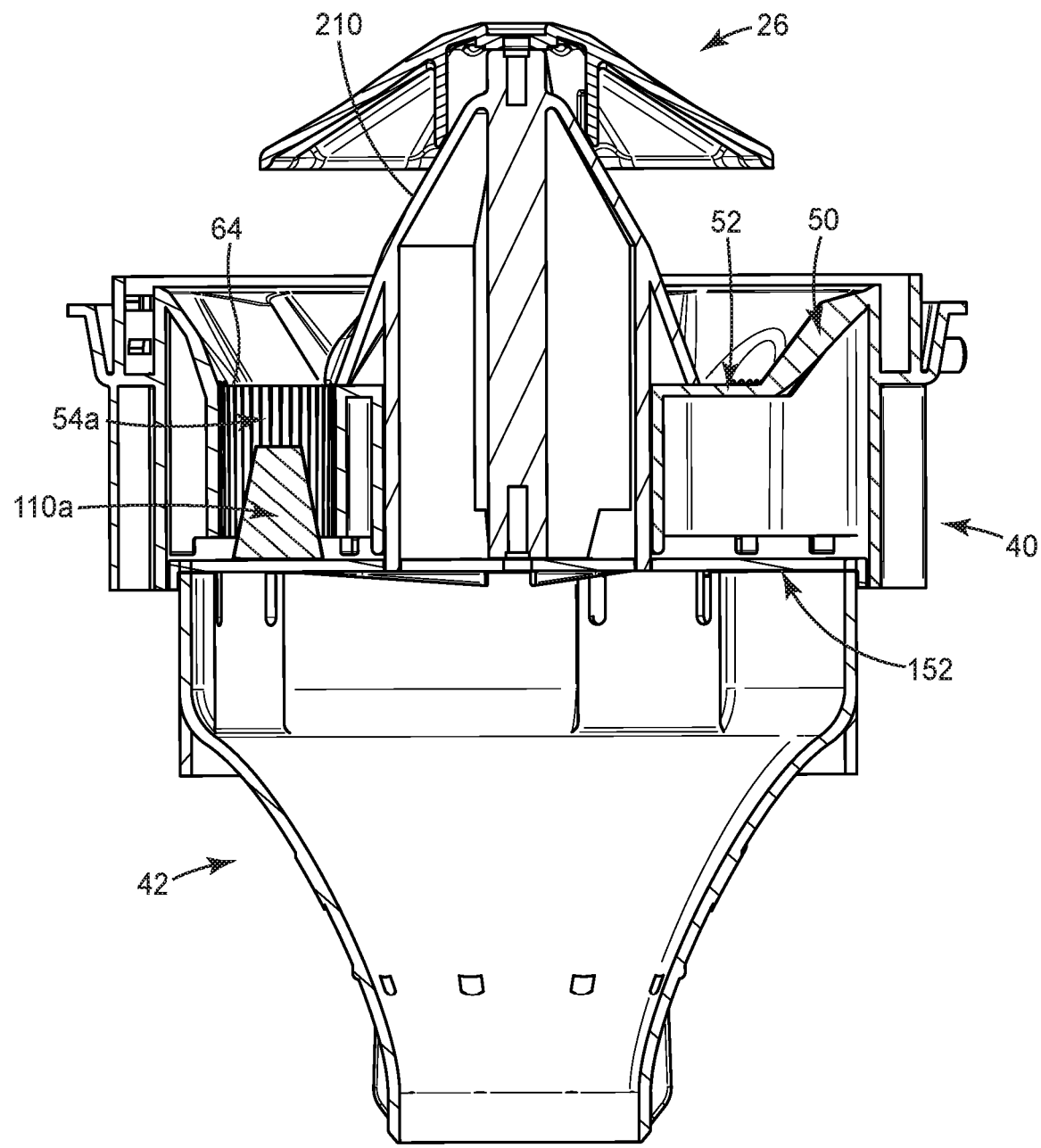

With rotation of the index assembly 42 (e.g., user-applied rotational force at the handle 150) relative to the separator assembly 40 (e.g., clockwise relative to orientation of FIG. 13A) and/or due to gravity, the first un-loaded earplug 110a becomes aligned with and self-loads into the first bore 54a. For example, rotation of the mixing body 154 directly causes the first un-loaded earplug 110a to move toward the first bore 54a and/or the mixing body 154 is in contact with other un-loaded earplugs within the well 56 and rotation of the mixing body 154 causes an entire grouping of un-loaded earplugs, including the first un-loaded earplug 110a, to move toward the first bore 54a. As the first un-loaded earplug 110a is caused to slide, roll, or otherwise articulate along the guide face 66, the first un-loaded earplug 110a progresses from the channel region 82 to the ramp region 80 associated with the first bore 54a. Once in the channel region 80, the first un-loaded earplug 110a interfaces with the corresponding trough 70 as shown in FIGS. 13C and 13D. In this regard, a radial distance between guide face 66 (along the trough 70) and the exterior surface 210 of the mixing body 154 tapers in a direction of the platform 52, allowing the earplug 110a to drop (due to gravity) toward the entrance opening 64 of the first bore 54a. Further, a shape of the trough 70 assists in guiding the earplug 110a to slide directly into the bore 54a in an upright or lengthwise manner. The trough 70 encourages the individual earplug 110a to readily drop into the open bore 54a, and as the earplug 110a drops or slides along either the trough 70 or the exterior surface 210 of the mixing body 154 (or both), the earplug 110a is naturally oriented lengthwise. Once inside the bore 54a (FIG. 13D), the earplug 110a can rest on the plate 152, sliding along a surface of the plate 152 as the index assembly 42 is further rotated.

Figure 14A:
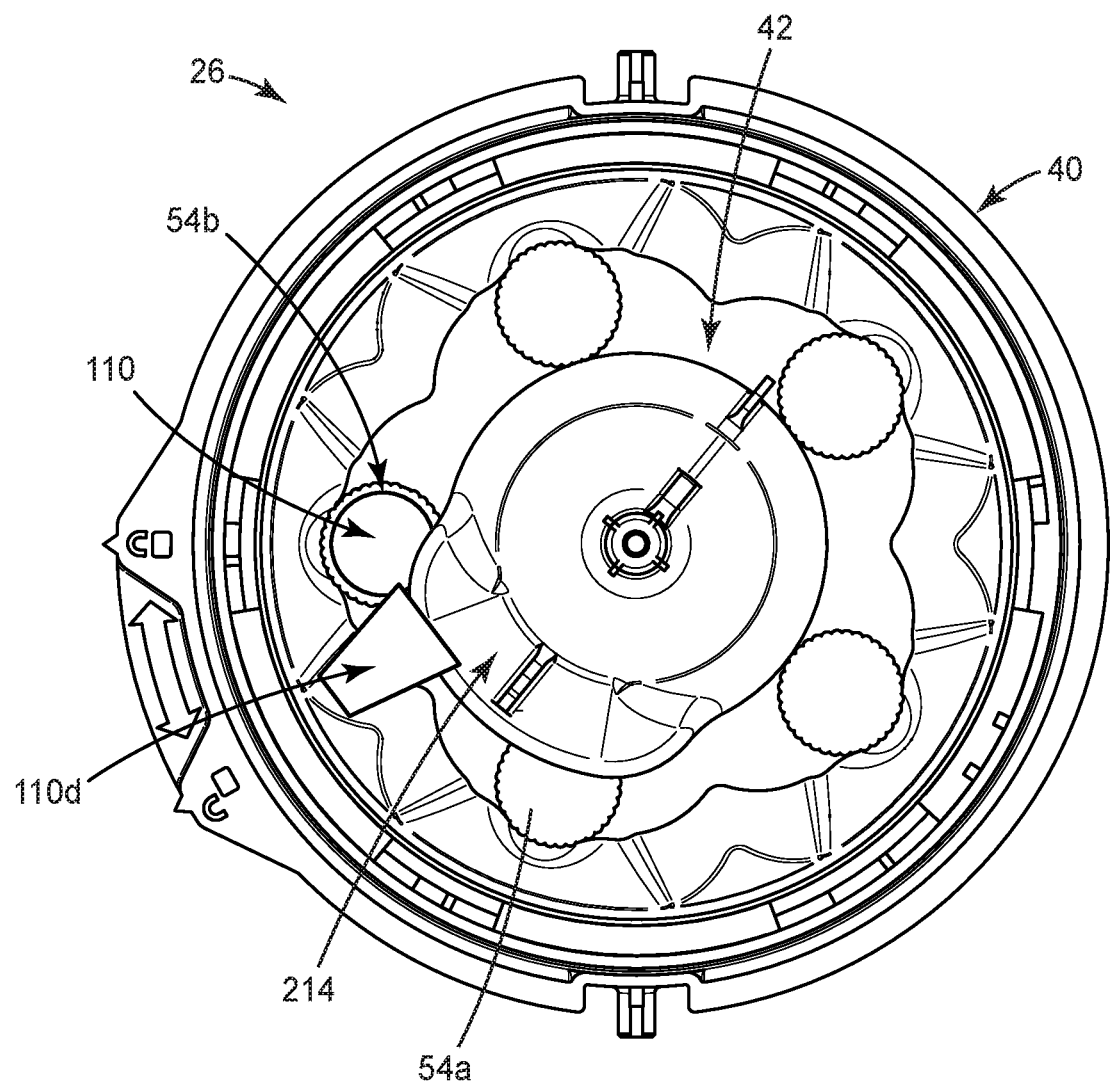
FIGS. 14A-14D illustrate operation of the dispensing mechanism of FIG. 2A in dispensing disposable earplugs.
Figure 14B:
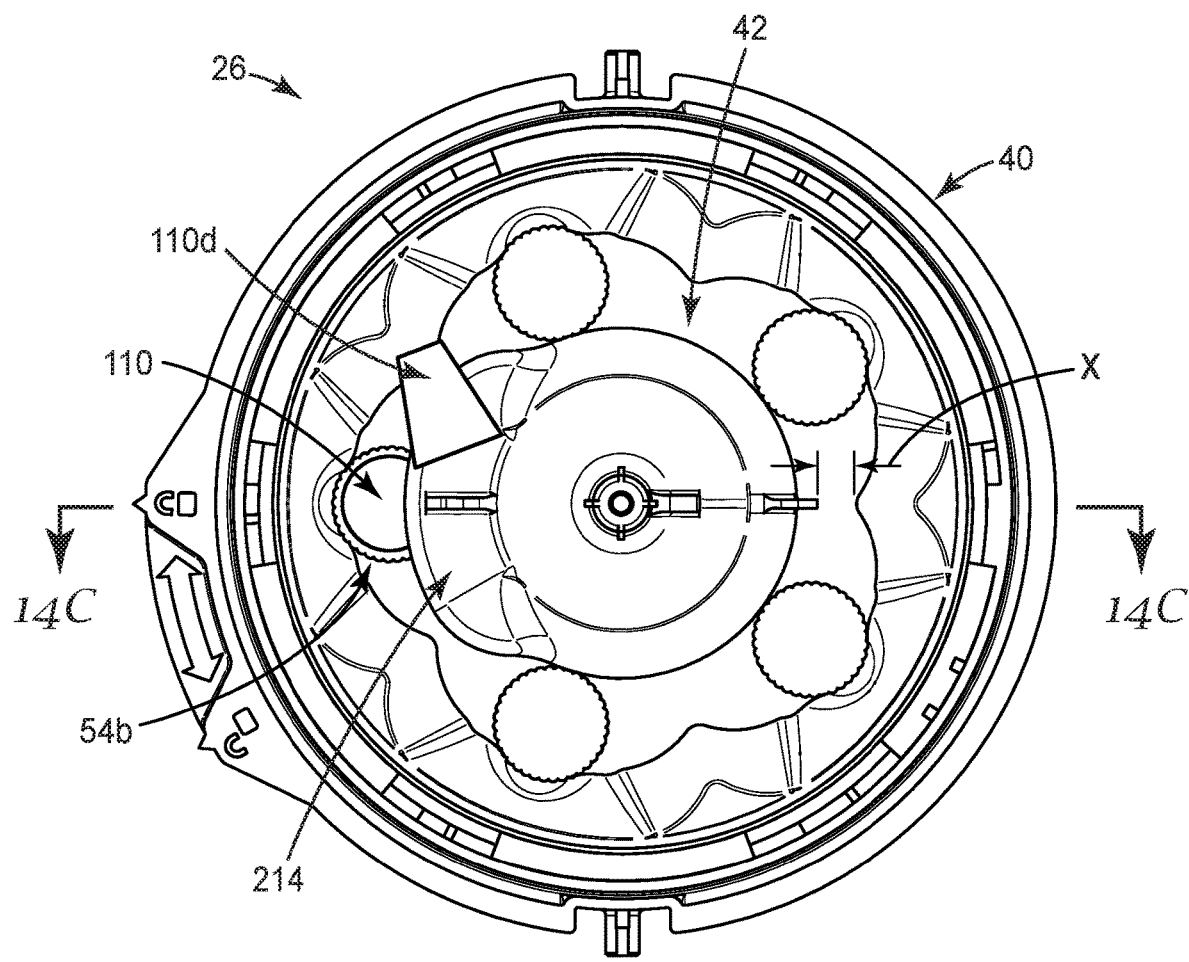
Figure 14C:
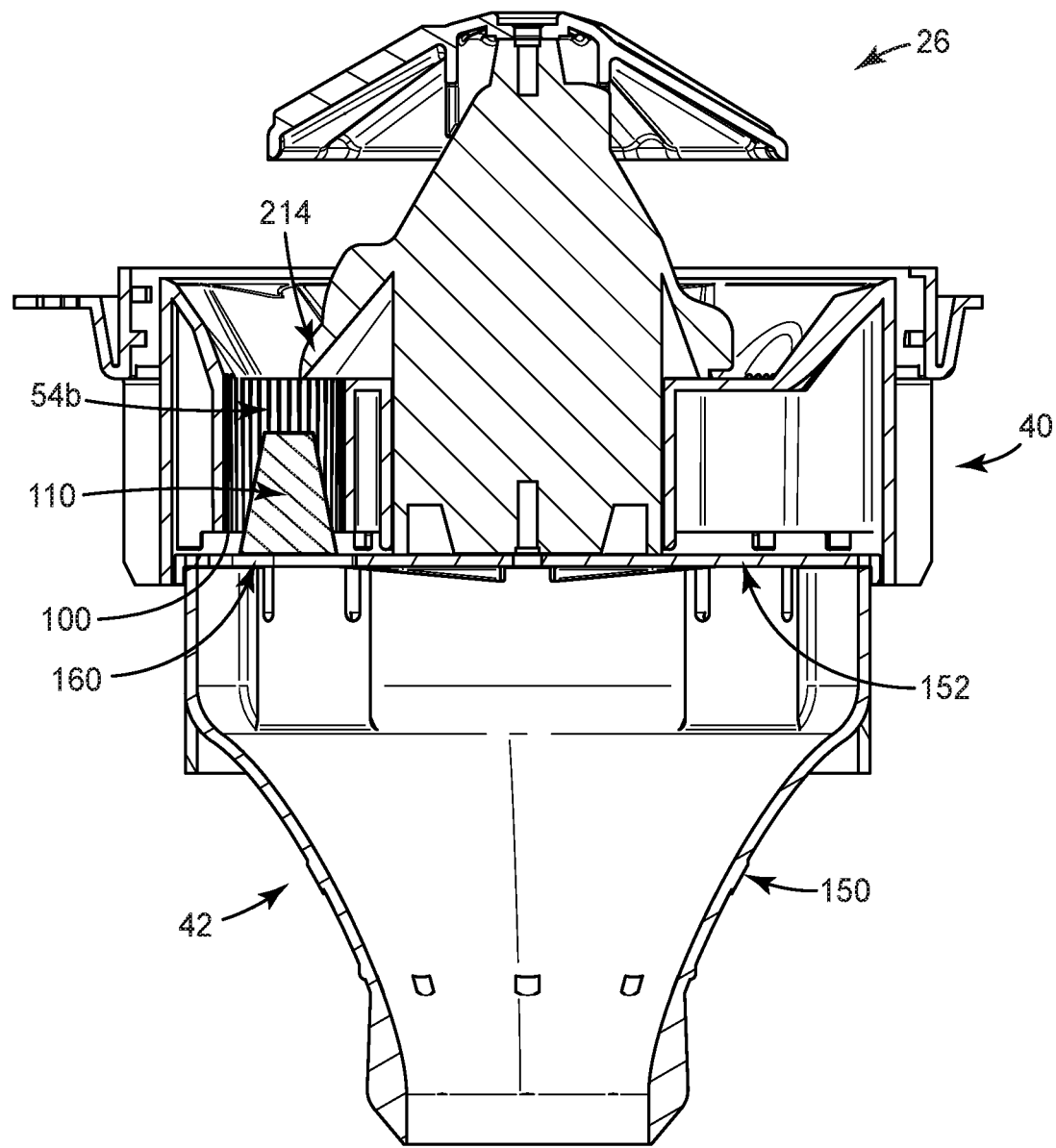

Operation of the dispensing unit 26 in dispensing an earplug from one of the bores 54 can initially be described with reference to the arrangement of FIG. 14A. In the state of FIG. 14A, an earplug 110 has previously been loaded into the second bore 54b, and the index assembly 42 is being rotated to move the paddle portion 214 from alignment with the first bore 54a into alignment with the second bore 54b (i.e., clockwise relative to the orientation of FIG. 14A). It will be recalled that the dispensing aperture 160 (FIG. 12C) is aligned with the paddle portion 214. Thus, in the specific arrangement of FIG. 14A, the dispensing aperture 160 is off-set from, or not otherwise aligned with, the second bore 54b such that the earplug 110 remains captured with the second bore 54b (and rests against the plate 152 (FIG. 12C)). As the index assembly 42 is further rotated (e.g., clockwise direction relative to FIG. 14A), the paddle portion 214 passes over and is brought into alignment with the second bore 54b, as is the dispensing aperture 160 (i.e., the dispensing aperture 160 is arranged so as to be open to the exit opening 100 of the second bore 54b) as reflected by FIGS. 14B and 14C. To the extent any un-loaded earplugs 110 (for example an unloaded earplug 110d identified in FIG. 14A) is in a vicinity of the entrance opening 64 of the second bore 54b, movement and presence of the paddle portion 214 ejects or clears the un-loaded earplugs 110 away from the platform 52 in a region of the second bore 54b as the paddle portion 214 is directed over the second bore 54b.

Figure 14D:
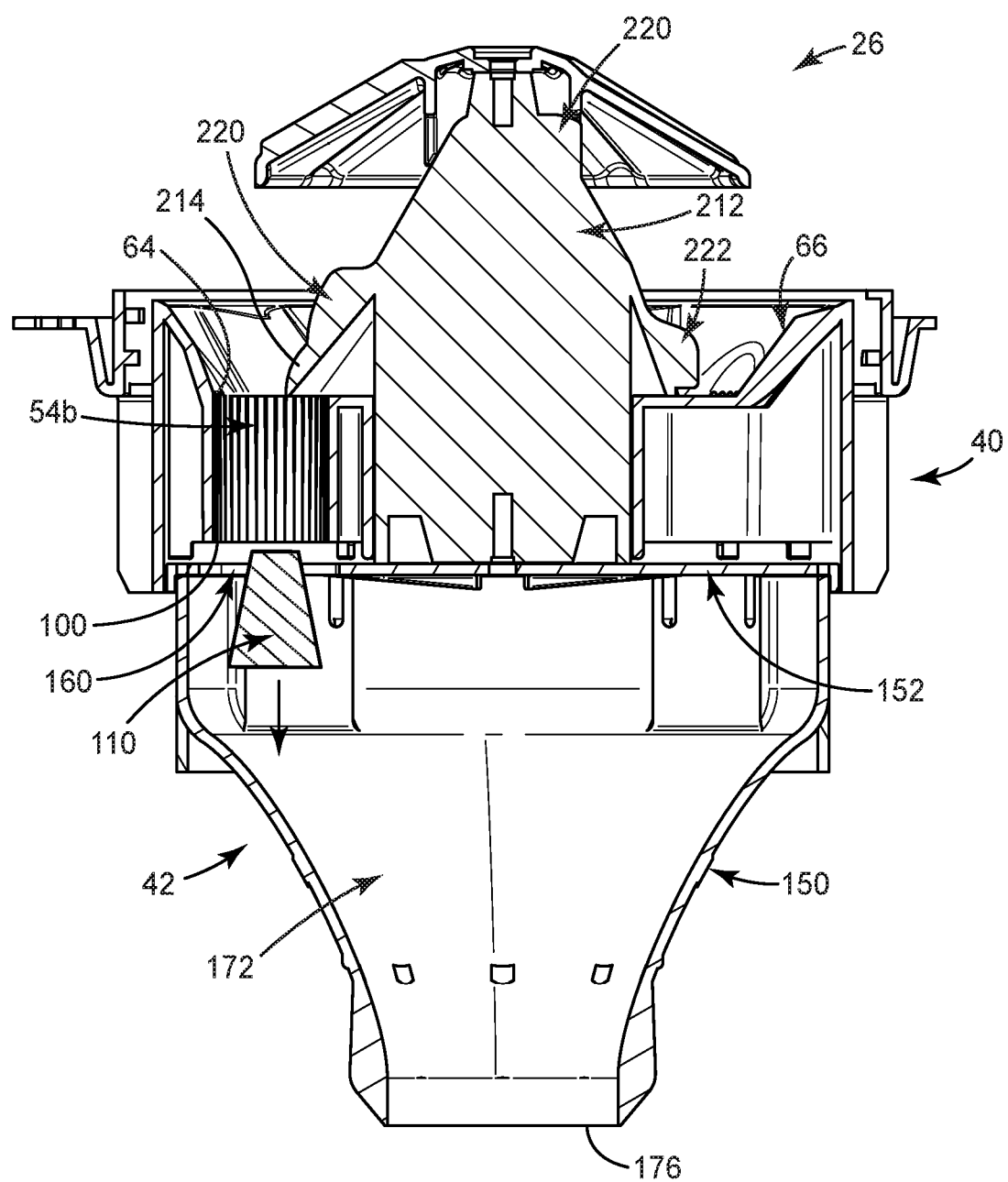

Once the index assembly 42 has been rotated relative to the separator assembly 40 so as to align the dispensing aperture 160 with the exit opening 100 of the second bore 54b, the earplug 110 is released from the second bore 54b and falls through the dispensing aperture 160 due to gravity as shown in FIG. 14D. The so-released earplug 110 then drops through the chamber 172 of the handle 150 (due to gravity) and is dispensed into a hand of the user at the dispensing end 176. With further, continued rotation of the index assembly 42, a new earplug 110 will self-load into the now-open second bore 54b (as the paddle portion 214 progresses beyond the entrance opening 64 of the second bore 54b so as to open the entrance opening 64 to the well 56) as described above for subsequent dispensing.

As evidenced by the above explanations, the dispensing mechanism 26 incorporates a number of novel features that promote accurate and consistent loading and dispensing of the earplugs 110 on an individual or singular basis. For example, the optional asymmetrical shape of the mixing body exterior surface 210 (as generated, for example, by the cone and paddle portions 212, 214) better ensures that only a single earplug 110 is dispensed with incremental rotation of the index assembly 42. Further, the optional wavy shape of the separator assembly guide face 66 consistently encourages or funnels the un-loaded earplugs 110 within the well 56 to become aligned with and drop into any open bore 54 in the upright or lengthwise orientation, while at the same time promoting more thorough mixing of the grouping of earplugs with rotation of the index assembly 42. The optional blades 220-224 provided with the mixing body 154 further enhance mixing. For example, a minimum distance X (FIG. 14B) between the second blade 222 and the guide surface 56 of the guide wall 50 (e.g., at the channel regions 82) is less than a diameter of the entrance openings 64 in some embodiments, and can approximate (or be smaller than) an expected diameter of the earplugs 110 to be handled by the dispensing mechanism 26. This optional dimensional relationship better ensures that the mixing body 154 (e.g., the second blade 222) will interface with free earplugs 110 within well 56 upon rotation of the index assembly 42.

Figure 15A:
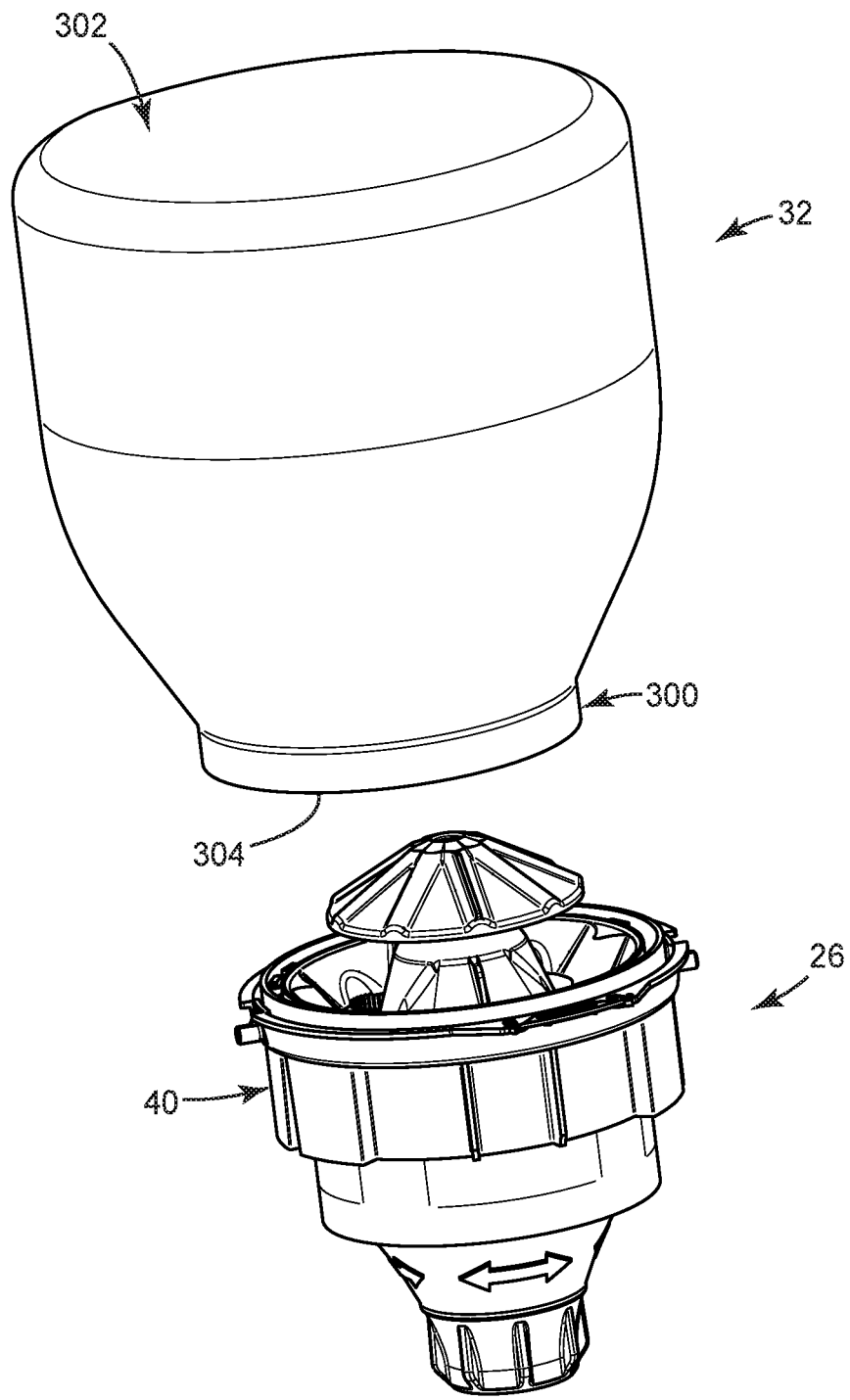
FIG. 15A is a perspective, exploded view of a portion of the dispenser of FIG. 1A, including the dispensing mechanism of FIG. 2A and a container.

While FIGS. 13A-14D reflect operation of the dispensing mechanism 26 relative to a few earplugs, it will be understood that the dispensing mechanisms of the present disclosure are useful in handling and dispensing individual earplugs from a bulk supply. For example, and as alluded to above, the separator assembly 40 is configured for selective assembly to a container of earplugs. With this in mind, FIG. 15A illustrates one embodiment of the container 32 relative to the dispensing mechanism 26. The container 32 can assume a wide variety of forms, and can be sized to contain any number of earplugs (not shown). Thus, the present disclosure is in no way limited to the container 32 as shown. In general terms, the container 32 provides an enclosed volume within which the supply of earplugs is retained. The container 32 forms a neck 300 opposite a floor 302. The neck 300 terminates at an open end 304 (referenced generally) that is open to the internal volume. As a point of reference, a cover (not shown) can be provided with the container 32 for temporarily closing the open end 304. Thus, for example, prior to mounting to the dispensing mechanism 26, the container 32 can be closed and stored in an upright orientation via the floor 302. Regardless, a size and shape of the neck 300 corresponds with geometric features provided with the separator mechanism 40 in a manner promoting releasable mounting of the container 32 to the dispensing mechanism 26.

More particularly, and with reference to FIG. 15B, releasable assembly of the container 32 to the dispensing mechanism 26 includes insertion of the neck 300 into the slot 140 provided with the separator assembly 40. A more robust connection between the container 32 and the dispensing mechanism 26 can be achieved via the optional locking tabs 141 (FIG. 3A) and/or other components. Regardless, a size and shape of the shield 156 is such that the neck 300 is easily introduced over the shield 156 and into engagement with the separator assembly 40. In some embodiments, a size and shape of the neck 300 corresponds with a shape and spatial location of the guide wall 50 such that upon final assembly, a tapering region 306 of the container 32 is generally aligned with the angular orientation of the guide wall 50 such that earplugs (not shown) within the container 32 naturally flow toward and along the guide wall 50.

Upon assembly of the container 32 to the dispensing mechanism 26, an effective storage volume 310 is collectively defined by the container 32 and the dispensing mechanism 26. The effective storage volume 310 includes an open volume of the container 32 and the well 56 of the dispensing mechanism 26. With this in mind, the shield 156, where provided, divides the effective storage volume 310 into two chambers. The first chamber 254, as described above, is established between the shield 156 and the platform 52. A second chamber 312 is established above the shield 156 (relative to the orientation of FIG. 15B). When the effective storage volume 310 is relatively full of the disposable earplugs 110 as shown in FIG. 15C, a first grouping 320 (referenced generally) of the earplugs 110 will naturally reside or accumulate within the first chamber 254, and a second grouping 322 (referenced generally) of the earplugs 110 will naturally reside or accumulate within the second chamber 312. That is to say, due to gravity, some of the earplugs 110 initially within just the container 32 will fall into the first chamber 254 as the container 32 is mounted onto the dispensing mechanism 26 (or, with an alternative mounting technique in which the container 32 is oriented with the neck 300 facing upwards and the dispensing mechanism 26 is placed on to the neck 300, some of the earplugs 110 within the container 32 will drop into the first chamber 254 as the assembled dispensing mechanism 26/container 32 is then rotated to the orientation of FIG. 15C).

As individual ones of the earplugs 110 of the first grouping 320 are incrementally dispensed from the first chamber 254 with operation of the dispensing mechanism 26 (as described above), various ones of the earplugs 110 of the second grouping 322 will naturally move from the second chamber 312 into the first chamber 254 due to gravity. However, the shield 156 effectively prevents a collective weight of the second grouping 322 from acting upon the first grouping 320 within the first chamber 254. As a result, the earplugs 110 within the first chamber 254 are more loosely maintained relative to one another, and thus can more easily be separated from one another (with rotation of the index assembly 42) and become guided or loaded into individual ones of the bores 54 (FIG. 3A) as described above. Further, the contoured surface 246 (FIG. 10A) and the blade 248 (FIG. 10B) of the shield 156 promotes mixing of the earplugs 110 in contact therewith during rotation of the index assembly 42.

Figure 16A:
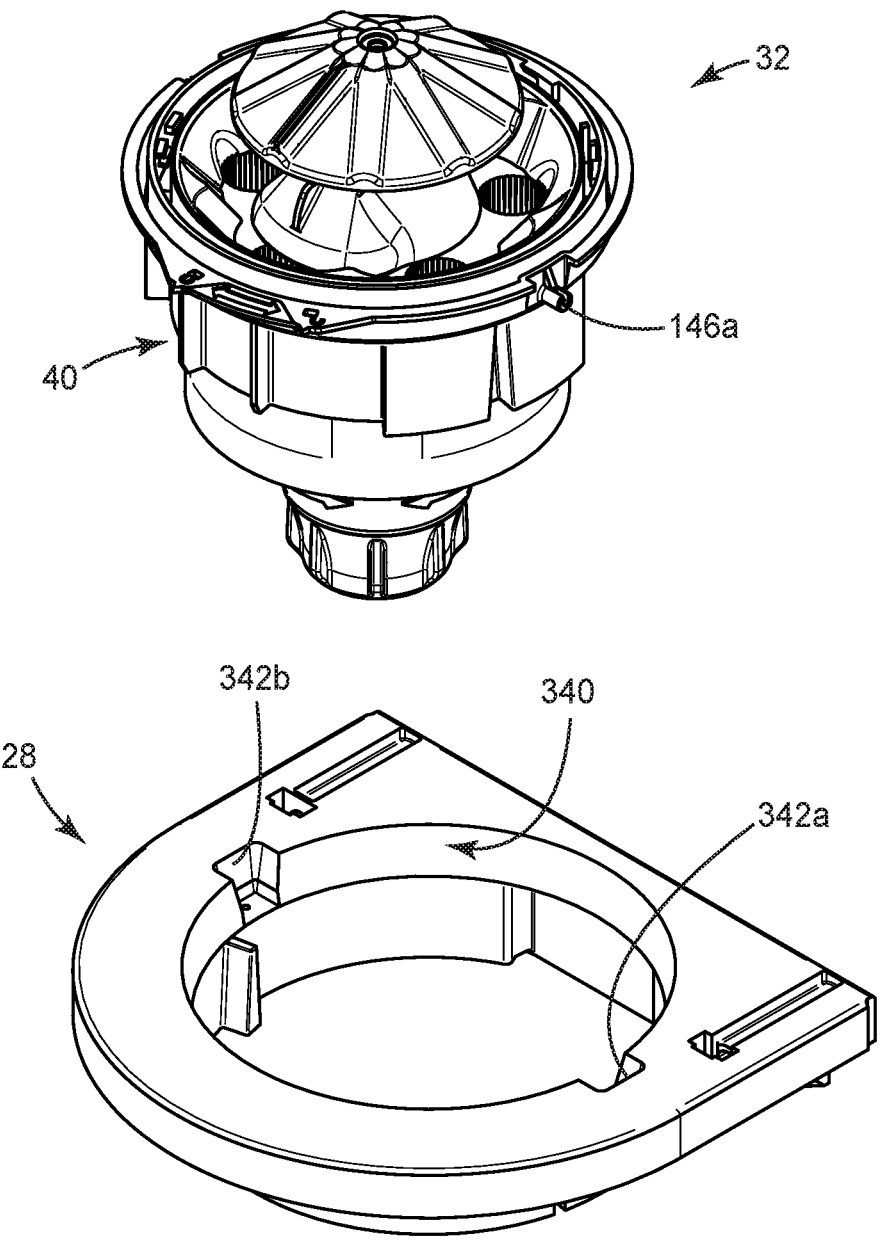
FIG. 16A is an exploded, perspective view of a dispensing unit useful with the dispenser of FIG. 1A, including the dispensing mechanism of FIG. 2A and a frame.
Figure 16B:
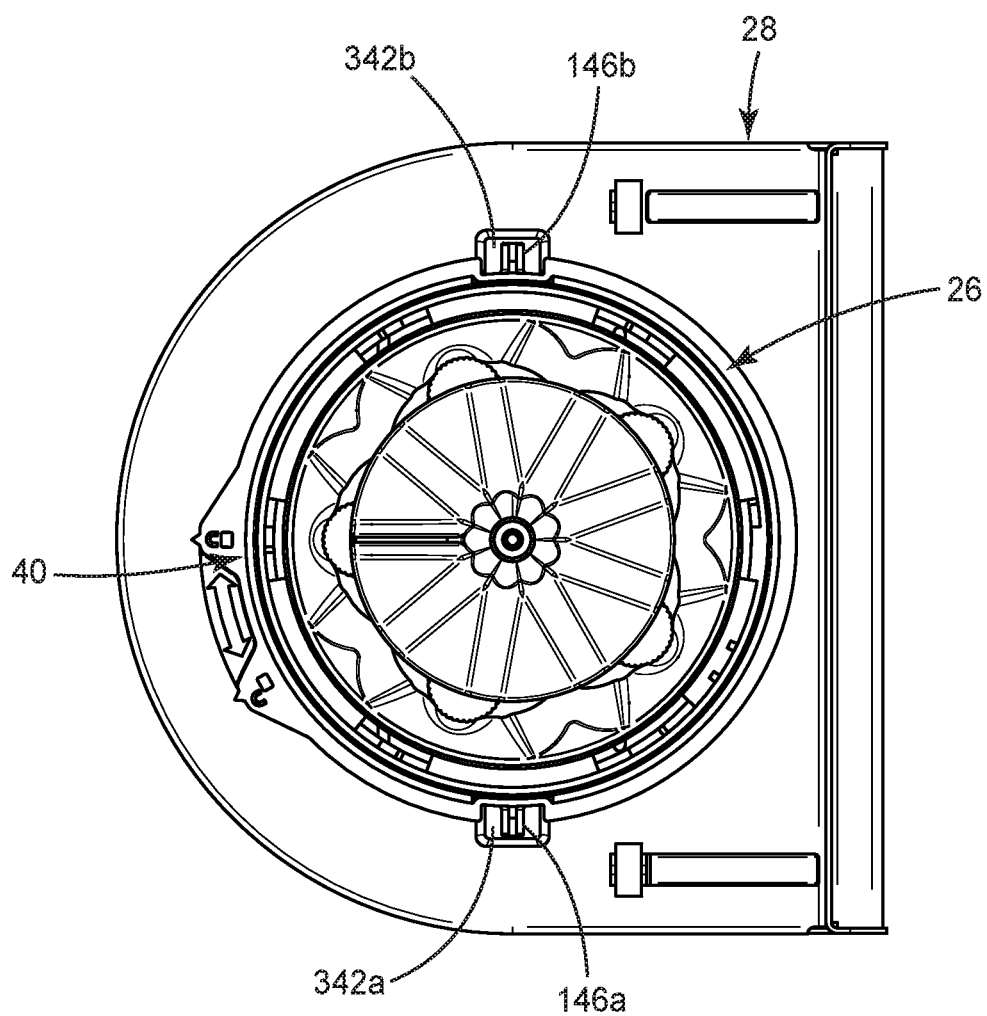
FIG. 16B is a top plan view of the components of FIG. 16A upon final assembly.

As indicated above, manual operation of the dispensing mechanism 26 generally entails user-caused rotation of the index assembly 42 relative to the separator assembly 40 (and thus relative to the bores 54). With this in mind, the dispensers of the present disclosure can include components that spatially retain the separator assembly 40 at a desired location and in a manner that spatially "holds" the separator assembly 40 during rotation of the index assembly 42. For example, FIG. 1A illustrates the frame 28 provided as part of the stand 30. As shown in FIG. 16A, the frame 28 forms a passage 340 that is sized and shaped to receive the separator assembly 40. In this regard, the frame 28 is optionally configured, in tandem with the separator assembly 40, such that the separator assembly 40 (and thus the dispensing mechanism 26) can be removably mounted to the passage 340. Moreover, the frame 28 and the separator assembly 40 incorporate complimentary features that fix the separator assembly 40 to the frame 28 such that the separator assembly 40 cannot rotate relative to the frame 28. For example, the frame 28 can form opposing cavities 342a, 342b sized and shaped to receive a respective one of the pins 146a, 146b (one of which is visible in FIG. 16A) provided with the separator assembly 40. With additional reference to FIG. 16B, upon placement of the pins 146a, 146b within the corresponding cavity 342a, 342b, the separator assembly 40 is thus supported by the frame 28, and cannot freely rotate relative to the frame 28. In some embodiments, clips (not shown) can be assembled to each of the pins 146a, 146b, respectively, and are configured to achieve a more robust, press fit-type coupling between the pins 146a, 146b and the frame 28. Alternatively, a wide variety of other mounting constructions are equally acceptable.

Figure 17:
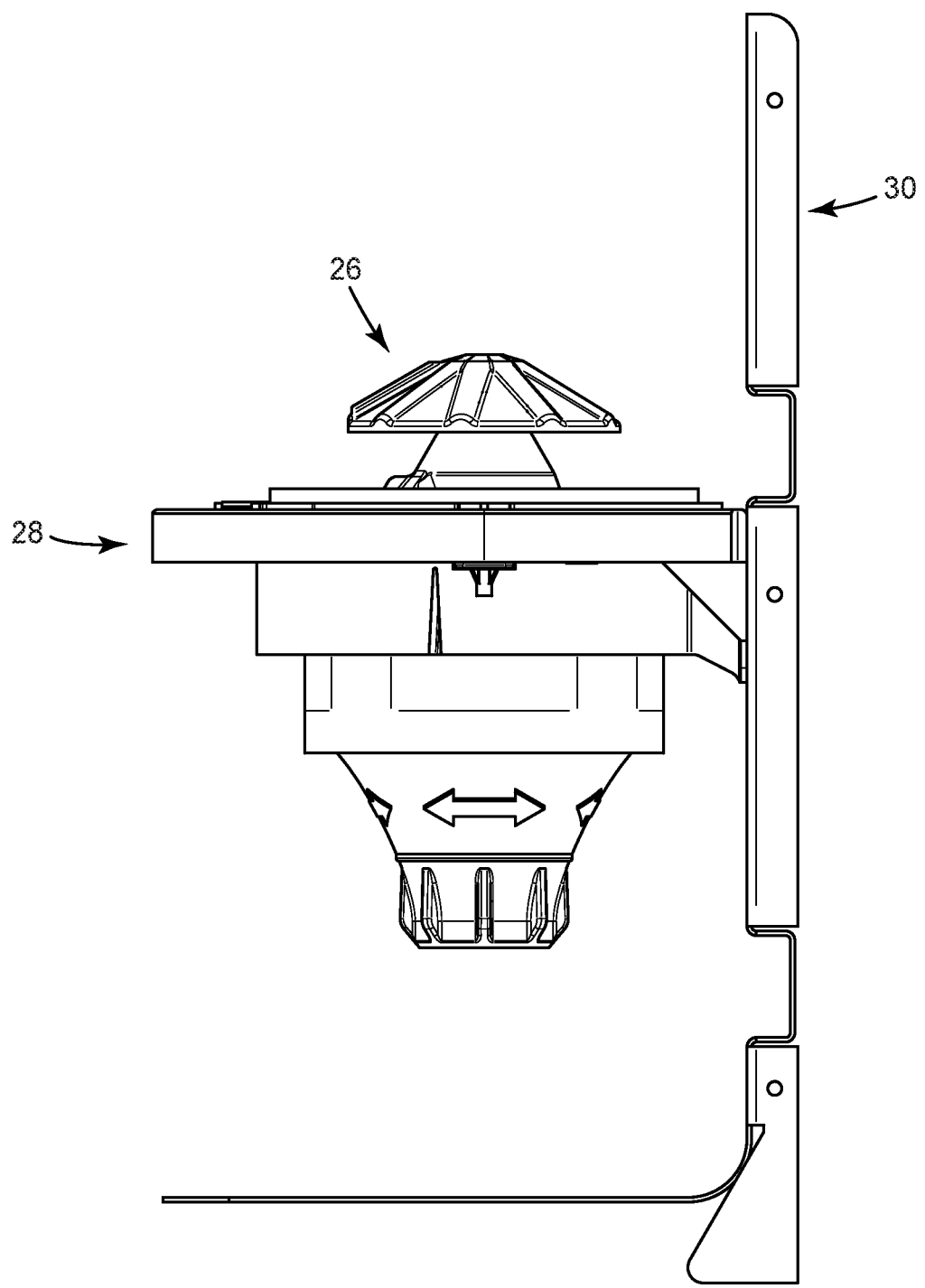
FIG. 17 is a side view of portions of the dispenser of FIG. 1A, including a dispensing mechanism, a frame, and a stand.

In some embodiments, the frame 28 can be directly assembled to a surface of interest (e.g., a vertical wall). In other embodiments, the frame 28 can be provided as part of the stand 30 that otherwise incorporates additional, optional structures that serve to support the frame 28 as shown in FIG. 1A. For example, the stand 30 can include or form a back wall 350 and a bottom wall 352. The frame 28 is coupled to the back wall 350 and arranged such that the bottom wall 352 projects underneath the frame 28. In some embodiments, the back wall 350 can incorporate various features that promote assembly to a vertical surface (e.g., a wall). Where provided, the bottom wall 352 serves as a catch for earplugs (not shown) released from the dispensing mechanism 26, and can include or form water drainage holes 354. In other configurations, the bottom wall 352 can be omitted. Final mounting of the dispensing mechanism 26 to the stand 30 is shown in FIG. 17.

Returning to FIGS. 1A and 1B, the dispensing unit 22 can optionally be further protected from the environment by the cover 24. The cover 24 includes or defines a front panel 360 and opposing side panels 362a, 362b. The front panel 360 forms an access opening 364 and a fill level opening 366. The side panel 362a, 362b are sized and shaped for assembly to the back wall 350 of the stand 30, with the access opening 364 being sized and shaped to facilitate insertion of a user's hand. The fill level opening 366 is located to promote viewing of components within the cover 24 as described below.

For example, and with specific reference to FIG. 1B, a user can obtain individual earplugs (not shown) by inserting his or her hand through the access opening 364 and grasping the handle 150. The user then rotates the handle 150 to cause a single earplug to be dispensed into the user's hand as described above. Notably, the cover 24 serves to protect the so-dispensed earplug from the surrounding environment (e.g., wind, rain, etc.). Moreover, the drainage holes 354 in the bottom wall 352 allow any water (e.g., rain) entering the access opening 364 to readily drain away. Thus, the dispenser 20 is highly amenable for installation at a plethora of different locations, including outdoor use. Finally, the fill level opening 366 is generally aligned with a portion of the container 32 (as assembled to the dispensing mechanism 26), thus allowing a user to visually estimate the quantity of earplugs remaining within the container 32.

The disposable earplug dispensing mechanisms and related earplug dispensers of the present disclosure provide a marked improvement over previous designs. The dispensing mechanism is easy to manually operate, and accurately dispenses earplugs from a bulk supply on an individual basis with minimal occurrences of jamming. Optional features, such as the asymmetric mixing body, the contoured guide surface, etc., promote consistent interface with compressible, tacky disposable earplugs.

The foregoing detailed description and examples have been given for clarity of understanding only. No unnecessary limitations are to be understood there from. It will be apparent to those skilled in the art that many changes can be made in the embodiments described without departing from the scope of the disclosure. Any feature or characteristic described with respect to any of the above embodiments can be incorporated individually or in combination with any other feature or characteristic, and are presented in the above order and combinations for clarity only. Thus, the scope of the present disclosure should not be limited to the exact details and structures described herein, but rather by the structures described by the language of the claims, and the equivalents of those structures.

What is claimed is:

1. A manually operable dispenser for dispensing earplugs from a container of earplugs, the dispenser including a dispensing mechanism defining a longitudinal axis and comprising:
   a stationary separator assembly including:
      a guide wall projecting from a platform to define a well for receiving earplugs from container,
      a plurality of circumferentially arranged bore structures each forming a bore extending from an entrance opening in the platform to an exit opening at a trailing side opposite the platform; and
   an index assembly rotatably coupled to the separator assembly, the index assembly including:
      a handle defining a longitudinal axis,
      a plate connected to the handle with the plate defining a dispensing aperture,
      a mixing body connected to the plate opposite the handle and having an upper end,
         a lower end, and an exterior surface defined, at least in part, by:
         a cone portion forming the exterior surface to taper in diameter from the lower end toward the upper end,
         a single paddle portion projecting radially, relative to the longitudinal axis, from the cone portion at the lower end,
         wherein the single paddle portion is configured to render the exterior surface of the mixing body asymmetrical by providing a radially-outward deviation from the lower end of the cone portion, which radially-outward deviation of the mixing body exhibits a radius that is greater than a radius of the lower end of the cone portion,
         wherein the mixing body further includes a first blade projecting from the cone portion opposite the paddle portion and wherein a distance between the first blade and at least a segment of the guide wall in a direction perpendicular to the longitudinal axis is less than a diameter of each of the bores and wherein the handle, the plate and the mixing body are configured so that the mixing body is on an opposite side of the plate from the handle;
   wherein at least the lower end is disposed within the well; and further wherein the dispenser is configured such that a manually-applied rotational force at the handle:

selectively aligns the dispensing aperture with the exit opening of individual ones of the bores, selectively arranges the paddle portion to at least partially cover the entrance opening of individual ones of the bores.

2. The dispenser of claim 1, wherein the plate is coupled to the handle such that the plate and the handle rotate in tandem relative to the separator assembly in response to a rotational force applied to the handle.

3. The dispenser of claim 2, wherein the mixing body is coupled to the plate such that the mixing body rotates in tandem with the plate and the handle relative to the separator assembly in response to a rotational force applied to the handle.

4. The dispenser of claim 1, wherein the paddle portion is longitudinally aligned with the dispensing aperture.

5. The dispenser of claim 1, wherein the dispenser is configured such that the paddle portion and the dispensing aperture are selectively aligned in tandem with the entrance and exit openings, respectively, of an individual one of the bores.

6. The dispenser of claim 1, wherein the plate is located proximate the trailing side of the bore structures such that when the dispensing aperture is aligned with the exit opening of a corresponding bore, an earplug located within the corresponding bore falls through the dispensing aperture.

7. The dispenser of claim 1, wherein at least the lower end, including the paddle portion, is disposed within the well.

8. The dispenser of claim 1, wherein the lower end is located proximate the platform such that when the paddle portion is arranged over the entrance opening of the corresponding bore, an earplug located within the well is prevented from dropping into the corresponding bore by the paddle portion.

9. The dispenser of claim 1, wherein the exterior surface is asymmetric in a plane passing through the paddle portion.

10. The dispenser of claim 1, wherein the exterior surface is asymmetric in a plane perpendicular to the longitudinal axis and passing through the paddle portion.

11. The dispenser of claim 1, wherein the exterior surface is asymmetric in a plane including the longitudinal axis and passing through the paddle portion.

12. The dispenser of claim 1, wherein the entrance openings are circumferentially arranged relative to one another and combine to collectively define a ring shape having an inner radius and an outer radius relative to the longitudinal axis upon final assembly, and further wherein upon final assembly a radius of the lower end along the cone portion relative to the longitudinal axis is less than the inner radius of the ring shape.

13. The dispenser of claim 12, wherein a radius of the lower end along the paddle portion relative to the longitudinal axis is greater than the inner radius of the ring shape.

14. The dispenser of claim 1, wherein the exterior surface has a circumferential shape along the paddle portion, and further wherein a circumferential length of the circumferential shape is greater than a diameter of each of the bores.

15. The dispenser of claim 1, wherein the mixing body further includes a second blade projecting from the paddle body at a location spaced from the lower end.

16. The dispenser of claim 15, wherein the mixing body further includes a third blade projecting from the cone portion proximate the upper end.

17. The dispenser of claim 1, wherein the index assembly further includes a shield connected to the mixing body approximate the upper end.

18. The dispenser of claim 17, wherein the shield includes a base disposed above the upper end opposite the lower end and shield wall projecting radially outwardly from the base to a perimeter edge having a diameter greater than a maximum diameter of the lower end.

19. The dispenser of claim 1, wherein the handle is a hollow body forming a chamber open to the dispensing aperture and to a dispensing end of the handle opposite the plate.

20. The dispenser of claim 19, wherein the dispenser is configured such that individual earplugs within the well are induced by gravity into respective ones of the bores, and an earplug within a respective one of the bores is induced by gravity into the dispensing aperture, then into the chamber, and then to the dispensing end upon alignment of the dispending aperture with the respective one of the bores.

21. The dispenser claim 19, further comprising:

a stand maintaining a frame sized to support the separator assembly above a surface such that upon mounting of the separator assembly to the frame, the handle extends below the frame and the separator assembly is held stationary with rotation of the index assembly.

* * * * *

UNITED STATES PATENT AND TRADEMARK OFFICE
CERTIFICATE OF CORRECTION

PATENT NO. : 10,482,703 B2
APPLICATION NO. : 15/320673
DATED : November 19, 2019
INVENTOR(S) : David Rudek Page 1 of 1

It is certified that error appears in the above-identified patent and that said Letters Patent is hereby corrected as shown below:

In the Specification

Column 9
Line 34, delete "flouropolymer" and insert -- fluoropolymer --, therefor.

In the Claims

Column 22
Line 38, in Claim 20, delete "dispending" and insert -- dispensing --, therefor.
Line 39, in Claim 21, after "dispenser" insert -- of --.

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*